(12) United States Patent
Lei et al.

(10) Patent No.: US 7,947,814 B2
(45) Date of Patent: *May 24, 2011

(54) METAL COMPLEXES OF POLYDENTATE BETA-KETOIMINATES

(75) Inventors: Xinjian Lei, Vista, CA (US); Michael Ulman, Mertztown, PA (US); Liam Quinn, Encinitas, CA (US); Hansong Cheng, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 961 days.

This patent is subject to a terminal disclaimer.

(21) Appl. No.: 11/735,603

(22) Filed: Apr. 16, 2007

(65) Prior Publication Data

US 2007/0248754 A1 Oct. 25, 2007

Related U.S. Application Data

(60) Provisional application No. 60/794,820, filed on Apr. 25, 2006.

(51) Int. Cl.
*C07F 5/00* (2006.01)
(52) U.S. Cl. .......................................................... 534/15
(58) Field of Classification Search ...................... 534/15
See application file for complete search history.

(56) References Cited

U.S. PATENT DOCUMENTS

| | | | |
|---|---|---|---|
| 5,782,986 | A | 7/1998 | Butterbaugh et al. |
| 5,820,664 | A | 10/1998 | Gardiner et al. |
| 7,691,984 | B2 * | 4/2010 | Lei et al. .......................... 534/15 |
| 7,723,493 | B2 * | 5/2010 | Lei et al. .......................... 534/15 |
| 2005/0170092 | A1 | 8/2005 | Benvenuti et al. |
| 2007/0248754 | A1 | 10/2007 | Lei et al. |

FOREIGN PATENT DOCUMENTS

| | | |
|---|---|---|
| EP | 369297 B1 | 8/1993 |
| EP | 1227079 A2 | 7/2002 |
| EP | 1 676 849 A | 7/2006 |
| EP | 1 676 849 A1 | 7/2006 |
| EP | 1 676 850 A | 7/2006 |
| JP | 02-188564 A | 7/1990 |
| JP | 03-163055 A | 7/1991 |
| JP | 6-298714 A | 10/1994 |
| JP | 06-298714 A | 10/1994 |
| JP | 08-259528 A | 10/1996 |
| JP | 2000-503805 A | 3/2000 |
| JP | 2002-193988 A | 7/2002 |
| JP | 2002-302473 A | 10/2002 |
| JP | 2004-014813 A | 1/2004 |
| JP | 2005-531619 A | 10/2005 |
| KR | 10-2009-0007099 A | 4/2007 |
| KR | 10-2009-0007102 A | 4/2007 |
| TW | 200403249 B | 3/2004 |
| TW | 1256078 | 6/2006 |
| TW | 1256078 B | 6/2006 |
| WO | 02/18394 A1 | 3/2002 |
| WO | 2004002946 A1 | 1/2004 |

OTHER PUBLICATIONS

Douglas L Schulz, et al, New Precursors for Barium MOCVD, Inorg. Chem., 1993, 249-250, 32, 3, Amer. Chem. Soc.
Sergej Pasko, et al, Synthesis and Characterization of New Alkaline Earth Metal B-ketoiminates. Inorg. Chem., 2005, 483-487, 8, Elsevier B.V.
Pier Luigi Franceschini, et al, Volatile B-Ketoiminato- and B-Diketiminator-Based Zirconium Complexes as Potential MOCVD Precursors, Inorg. Chem., 2003, 7273-7282, 42, Amer. Chem. Soc.
Tsung-Yi Chou, et al, Synthesis and Characterization of Tris (B-ketoiminator) ruthenium(III) Complexes: . . . Chem. Vap. Deposition, 2004, 10, 3, 149-158.
Sunkwon Lim, et al, A Study on the Development of Chemical Vapor Deposition Precursors. 4. Synthesis and . . . Chem. Mater., 2002, 14, 1548-1554, Amer. Chem. Soc.
Sunkwon Lim, et al, A Study on the Development of CVD Precursors V—synthesis and Characterization of new N-alkoxy-B-ketoiminate Comlexes of Titanium, Jour. Organ. Chem., 2004, 689, 224-237, Elsevier B.V.
Nikki L. Edleman, et al, Synthesis and Characterization of Volatile, Fluorine-Free B-Ketoiminate Lanthanide MOCVD Precursors and Their Implementation In . . . Inorg. Chem., 2002, 41, 5005-5023, Amer. Chem. Soc.

(Continued)

*Primary Examiner* — Michael G Hartley
*Assistant Examiner* — James W Rogers
(74) *Attorney, Agent, or Firm* — Lina Yang

(57) ABSTRACT

A plurality of metal-containing complexes of a polydentate beta-ketoiminate, one embodiment of which is represented by the structure are shown:

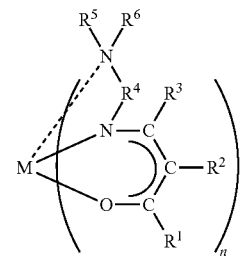

wherein M is a metal such as calcium, strontium, barium, scandium, yttrium, lanthanum, titanium, zirconium, vanadium, tungsten, manganese, cobalt, iron, nickel, ruthenium, zinc, copper, palladium, platinum, iridium, rhenium, osmium; wherein $R^1$ is selected from the group consisting of alkyl, fluoroalkyl, cycloaliphatic, and aryl, having from 1 to 10 carbon atoms; $R^2$ can be from the group consisting of hydrogen, alkyl, alkoxy, cycloaliphatic, and aryl; $R^3$ is linear or branched selected from the group consisting of alkylene, fluoroalkyl, cycloaliphatic, and aryl; $R^4$ is an alkylene bridge; $R^{5-6}$ are individually linear or branched selected from the group consisting of alkyl, fluoroalkyl, cycloaliphatic, aryl, and they can be connected to form a ring containing carbon, oxygen, or nitrogen atoms; n is an integer equal to the valence of the metal M.

45 Claims, 9 Drawing Sheets

OTHER PUBLICATIONS

Daniel B. Studebaker, et al, Encapsulating Bis(B-Ketoiminator) Polyethers, Volatile, Fluorine-Free Barium Precursors for Metal . . . Inorg. Chem. 2000, 39, 3148-3157, Amer. Chem. Soc.

Jason S. Matthews, et al, Group 2 Element Precursors for the Chemical Vapor Deposition of Electronic Materials, Adv. in Inorg. Chem., 50, 2000, 173-192, Academic Press.

Edwards D.A., et al; "Aerosol-Assisted Chemical Vapour Deposition (AACVD) of Silver Films from Triphyenylphospine Adducts of Silver .Beta.-diketonates and .Beta.-diketoiminates, Including the Structure of [Ag(hfac)(PPh3)]"; Journal of Materials Chemistry; vol. 9, No. 8; 1999; pp. 1771-1780; XP002372344.

Bouquillon S, et al; "Simultaneous Generation of Anionic and Neutral Palladium(II) Complexes from Eta3-Allylpalladium Chloride Dimer and Fluorinated Beta-Enaminones"; European Journal of Organic Chemistry; No. 24; 2003; pp. 4714-4720; XP002372342.

Tung Y-L, et al; "Synthesis and Characterization of Allyl(Beta-Ketoiminato)Palladium (II) Complexes: New Precursors for Chemical Vapor Deposition of Palladium Thin Films"; Organometallics; vol. 18, No. 5; Feb. 5, 1999; pp. 864-869; XP002372343.

Collier W, et al; "Kinetics of Acid Hydrolysis of Nickel(II) and Copper(II) Compounds with the Cyclic Diamines 1,5-Diazocane, and 4,4-Dimethyl-7-(5,5,7-Trim Ethyl-1,4-Diazepan-1-YI)-5-Azaheptan-2-O1"; Australian Journal of Chemistry; vol. 42, No. 9; 1989; pp. 1611-1616; XP009089097.

Konefal E, et al; "Coordination Modes of Polydentate Ligands. 1. Template Synthesis of Complexes of Nickel(2+), Copper(2+), and Cobalt(2+) with Pentadentate and Hexadentate Ligands: Structure of a Highly Distorted Six-Coordinate Cobalt(2+) Complex"; Inorganic Chemistry; vol. 23, No. 5; 1984; pp. 538-545; XP009079427.

Curtis N.F., et al; "Preparations, Magnetic Susceptibility and Structural Studies of Trinuclear Copper(II) Compounds of 4,4,9,9-Tetramethyl-5,8-Diazadodecane-2,11-Diol"; Australian Journal of Chemistry; vol. 41, No. 10; 1988; pp. 1545-1555; XP009089095.

Morgan, K.R., et al; "Preparation, and Complexes with Nickel(II) and Copper(II), of a Diazepane Amine Alcohol. The Structure of [4,4-Dimethyl-7-(5,5,7-Trimethyl-1,4-Diazepan-1-YI)-5-Azaheptan-2-O1]Nickel (II) Perchlorate"; Austrailian Journal of Chemistry; vol. 36, No. 7; 1983; pp. 1341-1351; XP009089096.

Martin J.W.L., et al; "Fluorinated Alkoxides. Part XIII. The Reduction of Beta-Imino-Alkoxy Complexes to give Stable, Polydentate, Amino Alcohols"; Canadian Journal of Chemistry; vol. 56, No. 23; 1978; pp. 2966-2969; XP009089101.

Loeb, S.J., et al; "Coordination Modes of Polydentate Ligands. 2. Template Synthesis of Four-, Five-, and Six-Coordinate Fluorinated Schiff-Base Complexes of Ni2+: Structure of an Octahedral Ni2+ Complex Containing Two Tridentate Ligands"; Inorganic Chemistry; vol. 23; 1984; pp. 1509-1512.

Becht, M., et al; "117. Synthesis Crystal Structure, and Thermal Behaviour of Some New Copper Complexes with Tridentate β-Iminoketone Ligands"; Helvetica Chimica Acta; 1994; vol. 77(5); pp. 1288-1298.

Matthews, J.S., et al; "CVD of MgO from a Mg(B-ketoiminate)2: Preparation, Characterization, and Utilization of an Intramolecularly Stabilized, Highly Volatile, Thermally Robust Precursor"; Chemical Vapor Deposition; vol. 6, No. 3; 2000; pp. 129-132.

Yun, Chi, PH.D.; "Design, Synthesis and Application of a New Chemical Vapor Deposition Precursor"; Chemistry Research Institute; Oct. 2004; Doctoral Dissertation; pp. 1-17.

* cited by examiner

METAL COMPLEXES OF POLYDENTATE BETA-KETOIMINATES

CROSS-REFERENCE TO RELATED APPLICATIONS

This Application claims the benefit of Provisional U.S. Patent Application No. 60/794,820 filed Apr. 25, 2006.

BACKGROUND OF THE INVENTION

The semiconductor fabrication industry continues to metal source containing precursors for chemical vapor deposition processes including atomic layer deposition for fabricating conformal metal containing films on substrates such as silicon, metal nitride, metal oxide and other metal-containing layers using these metal-containing precursors.

BRIEF SUMMARY OF THE INVENTION

This invention is directed to metal containing polydentate β-ketoiminates and solutions wherein the polydentate β-ketoiminates incorporate nitrogen or oxygen functionality in the imino group. The polydentate β-ketoiminates are selected from the group represented by the structures:

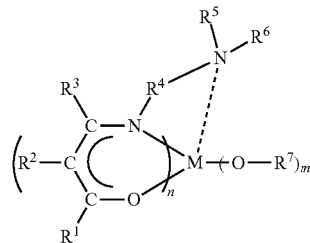

B wherein M is a metal ion selected from Group 4, 5 metals including titanium, zirconium, and hafnium; wherein $R^1$ is selected from the group consisting of alkyl, fluoroalkyl, cycloaliphatic, and aryl, preferably a group containing 1 to 6 carbon atoms; $R^2$ is selected from the group consisting of hydrogen, alkyl, alkoxy, cycloaliphatic, and aryl; $R^3$ is selected from the group consisting of alkyl, fluoroalkyl, cycloaliphatic, and aryl; $R^4$ is an alkylene bridge, preferably a group containing 2 or 3 carbon atoms, thus making a five- or six-membered coordinating ring to the metal center; $R^{5-6}$ are individually selected from the group consisting of alkyl, fluoroalkyl, cycloaliphatic, aryl, and they can be connected to form a ring containing carbon, oxygen, or nitrogen atoms; $R^7$ is selected from the group consisting of alkyl, fluoroalkyl, cycloaliphatic, and aryl; wherein m and n are at least 1 and the sum of m+n is equal to the valence of the metal.

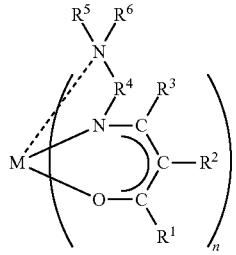

A

C wherein M is a metal having a valence of from 2 to 5. Examples of metals include calcium, strontium, barium, scandium, yttrium, lanthanum, titanium, zirconium, vanadium, tungsten, manganese, cobalt, iron, nickel, ruthenium, zinc, copper, palladium, platinum, iridium, rhenium, and osmium. A variety of organo groups may be employed as for example wherein $R^1$ is selected from the group consisting of alkyl, fluoroalkyl, cycloaliphatic, and aryl, having from 1 to 10 carbon atoms, preferably a group containing 1 to 6 carbon atoms; $R^2$ is selected from the group consisting of hydrogen, alkyl, alkoxy, cycloaliphatic, and aryl; $R^3$ is selected from the group consisting of alkyl, fluoroalkyl, cycloaliphatic, and aryl; $R^4$ is an alkylene bridge, preferably a group containing 2 or 3 carbon atoms, thus making a five- or six-membered coordinating ring to the metal center; $R^{5-6}$ are individually selected from the group consisting of alkyl, fluoroalkyl, cycloaliphatic, aryl, and they can be connected to form a ring containing carbon, oxygen, or nitrogen atoms. The subscript n is an integer and equals the valence of the metal M.

wherein M is an alkaline earth metal with specific examples including calcium, strontium, barium; $R^1$ is selected from the group consisting of alkyl, fluoroalkyl, cycloaliphatic, and aryl, preferably a group containing 1 to 6 carbon atoms; $R^2$ is selected from the group consisting of hydrogen, alkyl, alkoxy, cycloaliphatic, and aryl; $R^3$ is selected from the group consisting of alkyl, fluoroalkyl, cycloaliphatic, and aryl; $R^{4-5}$ are each a 2 carbon atom alkylene bridge, thus making a five-membered coordinating ring to the metal center; $R^{6-7}$ are individually selected from the group consisting of alkyl, fluoroalkyl, cycloaliphatic, aryl, or they can be connected to form a ring containing carbon, oxygen, or nitrogen atoms; and X is either an oxygen, or a nitrogen substituted with a hydrogen, an alkyl or an aryl group.

Several advantages can be achieved through these metal-containing polydentate β-ketoiminates as precursors for chemical vapor deposition or atomic layer deposition, and these include:

an ability to form reactive complexes in good yield;

an ability to form monomeric complexes, particularly strontium and barium complexes, coordinated with one kind of ligand, thus allowing one to achieve a high vapor pressure;

an ability to produce highly conformal metal thin films suited for use in a wide variety of electrical applications;

an ability to form highly conformal metal oxide thin films suited for use in microelectronic devices;

an ability to enhance the surface reaction between the metal-containing polydentate β-ketoiminates and the surface of a substrate due to the high chemical reactivity of the complexes; and, an ability to tune the physical property of these metal-containing polydentate β-ketoiminates via a change in the $R^{1-7}$ groups.

DETAILED DESCRIPTION OF THE DRAWINGS

DETAILED DESCRIPTION OF THE INVENTION

Figure 1:
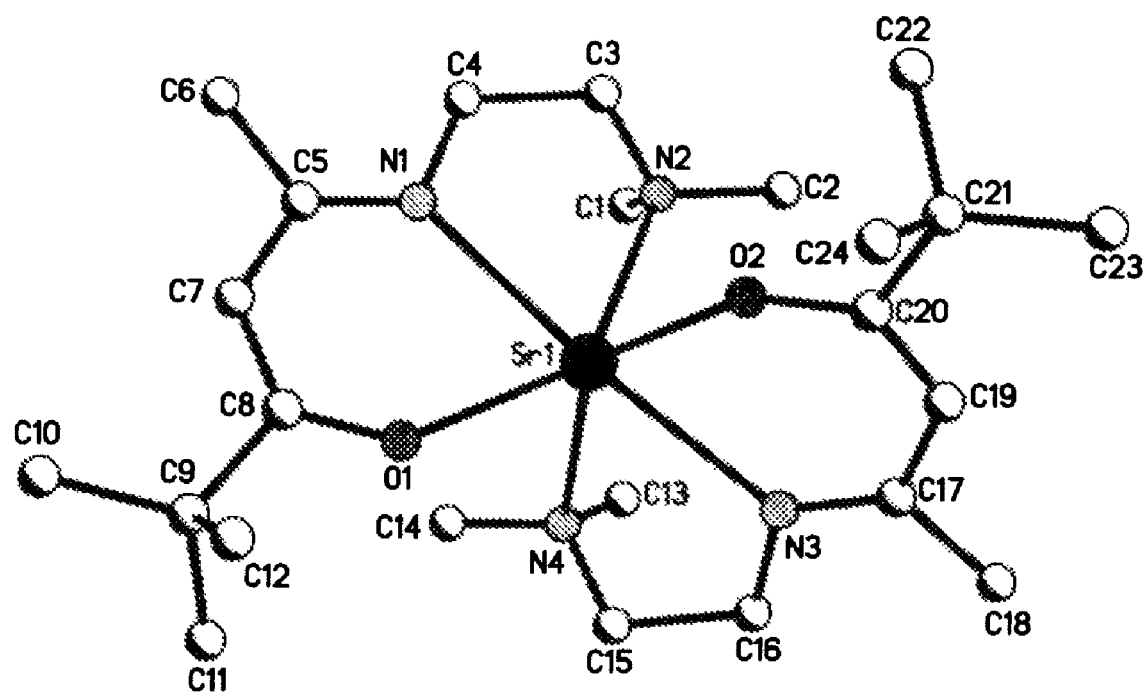
FIG. 1 is a drawing representative of the crystal structure of bis(2,2-dimethyl-5-(dimethylaminoethyl-imino)-3-hexanonato-N,O,N')strontium.

This invention is related to metal-containing polydentate β-ketoiminate precursors and their solutions which are useful for fabricating conformal metal containing films on substrates such as silicon, metal nitride, metal oxide and other metal layers via deposition processes, e.g., CVD and ALD. Such conformal metal containing films have applications ranging from computer chips, optical device, magnetic information storage, to metallic catalyst coated on a supporting material. In contrast to prior polydentate β-ketoiminate precursors, the polydentate β-ketoiminate ligands incorporate at least one amino organo imino functionality which is in contrast to the literatures reported alkoxy group as the donating ligand.

Oxidizing agents for vapor deposition process include oxygen, hydrogen peroxide and ozone and reducing agents for deposition processes include hydrogen, hydrazine, monoalkylhydrazine, dialkylhydrazine, and ammonia.

One type of structure in the metal precursor is illustrated in structure 1A below where the metal M has a valence of 2 having the formula:

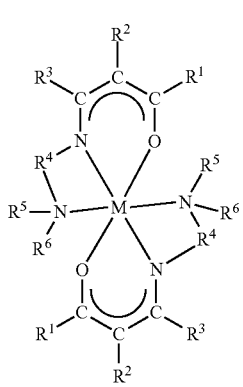

1A wherein M is selected from group 2, 8, 9, 10 metal atoms. In this precursor it is preferred that $R^1$ is a $C_{1-10}$ alkyl group, preferably a t-butyl or t-pentyl group when the metal is strontium and barium and $C_{1-5}$ when cobalt or nickel, $R^2$ is selected from the group consisting of hydrogen, $C_{1-6}$ alkyl, and $C_{6-10}$ aryl; $R^3$ is selected from the group consisting of $C_{1-6}$ alkyl, $C_{1-6}$ fluoroalkyl, $C_{6-10}$ aryl; $R^5$ and $R^6$ are individually lower $C_{1-3}$, preferably methyl groups and $R^4$ is a $C_{2-3}$ alkylene bridge, preferably an ethylene group. Preferred metals are calcium, strontium, barium, iron, cobalt, and nickel.

Another type of structure within the first class of metal complexes containing polydentater β-ketoiminate ligands is illustrated in structure 2A below where the metal M has a valence of 3 having the formula:

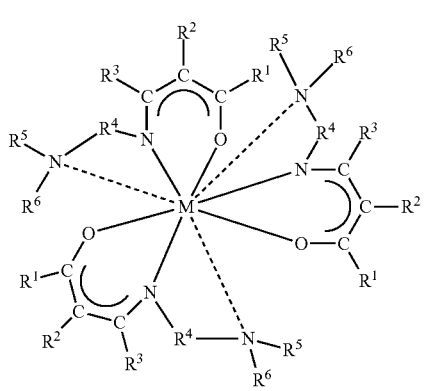

2A wherein M is selected from group 3 metal atoms. In this precursor it is preferred that $R^1$ is a $C_{4-6}$ alkyl group, preferably a t-butyl and t-pentyl group, $R^2$ is selected from the group consisting of hydrogen, $C_{1-6}$ alkyl, and $C_{6-10}$ aryl; $R^3$ is selected from the group consisting of $C_{1-6}$ alkyl, $C_{1-6}$ fluoroalkyl, $C_{6-10}$ aryl; $R^5$ and $R^6$ are individually lower $C_{1-3}$ alkyl, preferably methyl groups, and $R^4$ is a $C_{2-3}$ alkylene bridge, preferably an ethylene group. Preferred metals are scandium, yttrium, and lanthanum.

The second class of metal-containing precursors are comprised of polydentate β-ketoiminate ligands as shown in formula B:

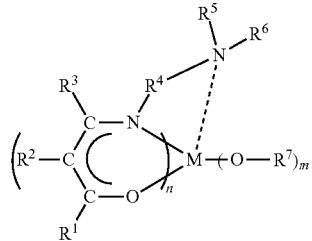

B wherein M is a Group 4 or 5 metal such as titanium, zirconium, or hafnium. As shown the complex consists of at least one alkoxy ligand and a polydentate β-ketoiminato ligand having at least one amino organo imino. The preferred $R^{1-6}$ groups are the same as in formula A. The preferred $R^7$ group is a linear or branched alkyl, e.g., iso-propyl, butyl, sec-butyl, and tert-butyl, m and n are at least 1 and the sum of m+n is equal to the valence of the metal The last class of metal-containing polydentate β-ketoiminate precursors are shown in formula C:

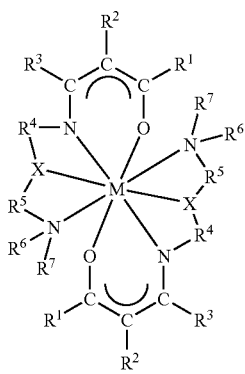

C wherein M is an alkaline earth metal wherein $R^1$ is selected from the group consisting of alkyl, fluoroalkyl, cycloaliphatic, and aryl, having from 1 to 10 carbon atoms; $R^{2-3}$ are individually selected from the group consisting of hydrogen, alkyl, alkoxy, cycloaliphatic, and aryl; $R^{4-5}$ are individually $C_{2-3}$ alkylene bridges, preferably ethylene groups, $R^{6-7}$ are individually selected from the group consisting of alkyl, fluoroalkyl, cycloaliphatic, aryl, and heterocyclic containing a oxygen, or nitrogen atom; X is either an oxygen, or nitrogen substituted with a hydrogen, an alkyl or an aryl group.

The polydentate β-ketoiminate ligands can be prepared by well known procedure such as the Claisen condensation of a bulky ketone and an ethyl ester in presence of a strong base such as sodium amide or hydride, followed by another known procedure such as Schiff base condensation reaction with alkylaminoalkylamine.

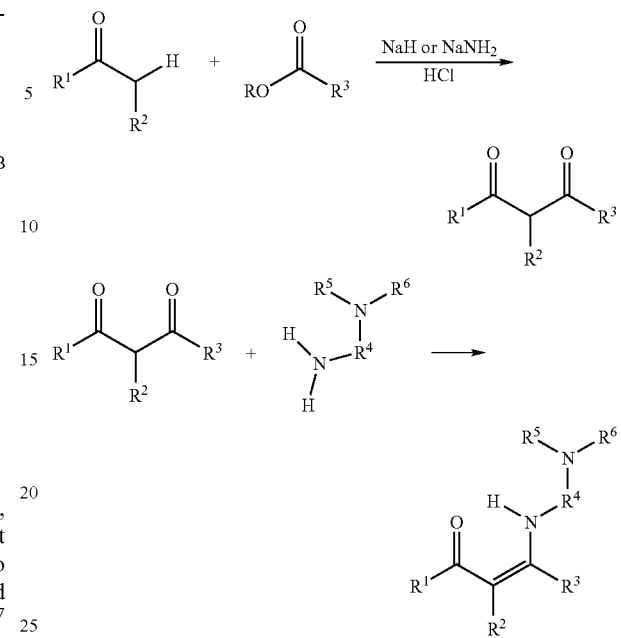

The ligands can be purified via vacuum distillation for a liquid or crystallization for solid.

As a preferred method for the formation of high yield polydentate ligands, it is preferred to choose a bulky $R^1$ group, e.g., $C_{4-10}$ alkyl groups without hydrogen attached to the carbon connected to the ketone functionality, most preferred $R^1$ group is tert-butyl or tert-pentyl. The $R^1$ group prevents side reactions occurring in the following Schiff condensation and later protecting the metal centers from intermolecular interaction. There is a competing issue and that is that the $R^{1-7}$ groups in the polydentate ligands should be as small as possible in order to decrease the molecular weight of the resulting metal-containing complexes and allow the achievement of complexes having a high vapor pressure. The preferred $R^{4-5}$ groups contain 2 to 3 carbon atoms in order to make the resulting complexes more stable via forming a five- or six-membered coordinating ring to the metal center.

The metal-containing complexes can then be prepared via the reaction of the resulting tridentate ligands with pure metal, metal amide, metal hydride, and metal alkoxide. The metal-containing complexes can also be prepared via reacting the polydentate ligand with alkyl lithium or potassium hydride to provide the lithium or potassium salt of the ligand, then followed by reaction with metal halide, $MX_2$ (X=Cl, Br, I). The group 4 and 5 mixed ligand complexes can be made via changing the ratio of metal alkoxide to the polydentate ligands.

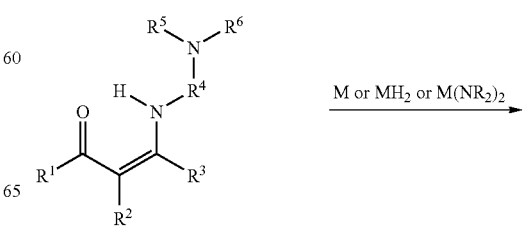

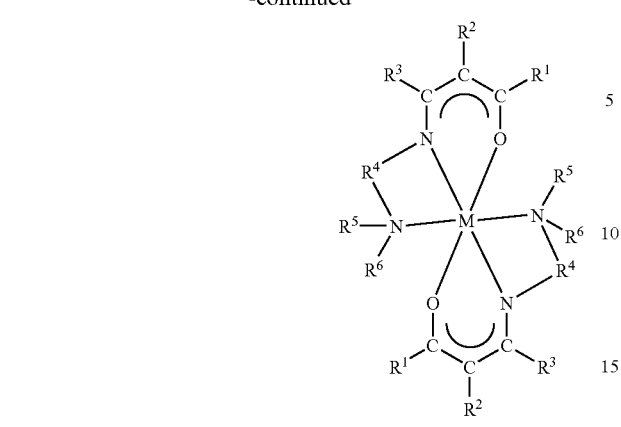
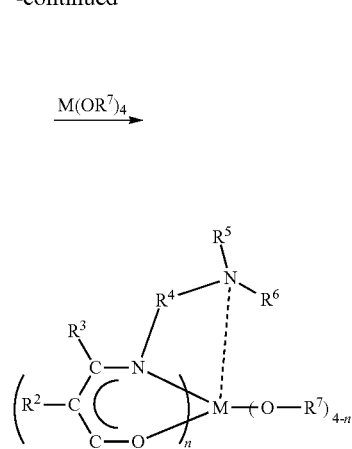
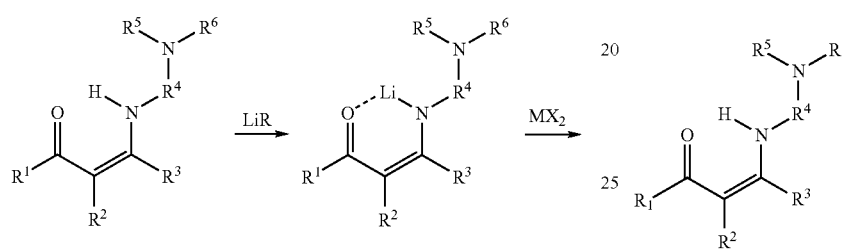
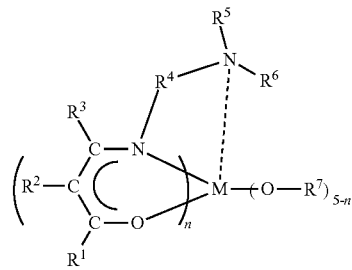
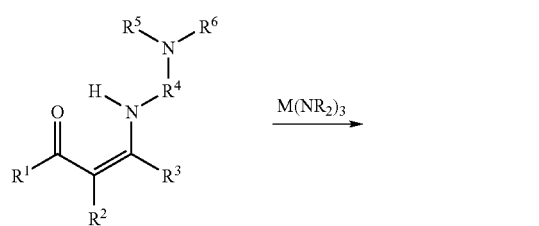
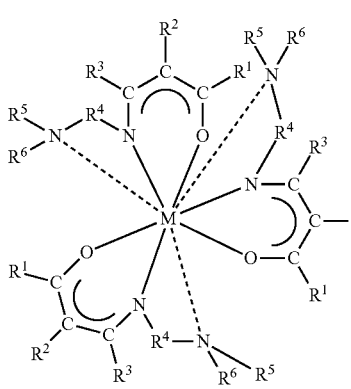

These metal-containing complexes with polydentate β-ketoiminate ligands can be employed as potential precursors to make thin metal or metal oxide films via either the chemical vapor deposition (CVD) or atomic layer deposition (ALD) method at temperatures less than 500° C. The CVD process can be carried out with or without reducing or oxidizing agents whereas an ALD process usually involves the employment of another reactant such as a reducing agent or oxidizing agent.

For multi-component metal oxide, these complexes can be premixed if they have the same polydentate β-ketoiminate ligands. These metal-containing complexes with polydentate β-ketoiminate ligands can be delivered in vapor phase into a CVD or ALD reactor via well-known bubbling or vapor draw techniques. A direct liquid delivery method can also be employed by dissolving the complexes in a suitable solvent or a solvent mixture to prepare a solution with a molar concentration from 0.001 to 2 M depending the solvent or mixed-solvents employed.

The solvent employed in solubilizing the precursor for use in a deposition process may comprise any compatible solvent or their mixture including aliphatic hydrocarbons, aromatic hydrocarbons, ethers, esters, nitrites, and alcohols. The solvent component of the solution preferably comprises a solvent selected from the group consisting of glyme solvents having from 1 to 20 ethoxy —$(C_2H_4O)$— repeat units; $C_2$-$C_{12}$ alkanols, organic ethers selected from the group consisting of dialkyl ethers comprising $C_1$-$C_6$ alkyl moieties, $C_4$-$C_8$ cyclic ethers; $C_{12}$-$C_{60}$ crown $O_4$-$O_{20}$ ethers wherein the prefixed $C_i$ range is the number i of carbon atoms in the ether compound and the suffixed $O_i$ range is the number i of oxygen atoms in the ether compound; $C_6$-$C_{12}$ aliphatic hydrocarbons; $C_6$-$C_{18}$ aromatic hydrocarbons; organic esters; organic amines, polyamines and organic amides.

Another class of solvents that offers advantages is the organic amide class of the form RCONR'R" wherein R and R' are alkyl having from 1-10 carbon atoms and they can be connected to form a cyclic group $(CH_2)_n$, wherein n is from 4-6, preferably 5, and R" is selected from alkyl having from 1 to 4 carbon atoms and cycloalkyl. N-methyl and N-cyclohexyl 2-pyrrolidinones are examples.

The following example illustrates the preparation of the metal-containing complexes with polydentate β-ketoiminate ligands as well as their use as precursors in metal-containing film deposition processes.

EXAMPLE 1

Synthesis of 2,2-dimethyl-5-(dimethylaminoethyl-imino)-3-hexanone

In a 500 mL Schlenk flask, 29.3 g (206 mmol) of 2,2-dimethyl-3,5-hexanedione and 24 g (170 mmol) anhydrous $Na_2SO_4$ were loaded with 200 mL THF. To the flask, 20.08 g (228 mmol) 3-(dimethylamino)ethylamine in 20 mL of THF was dropwise added. The reaction mixture was stirred for three days. Upon completion, the GC/MS analysis of the reaction mixture indicated the reaction was complete with trace amount 3-(dimethylamino)ethylamine. All volatiles were removed by distillation at temperature below 130° C. Subsequently the resulting slight yellow solution was vacuum distilled via a short-path apparatus. Crystallization from hexanes provided about 36 g of a white crystal with a yield of 82%. GC analysis of the crystals dissolved in hexane only shows one observable GC peak besides the hexane. The solid crystals were found to have a melting point of 28-30° C.

$^1$H NMR (500 MHz, $C_6D_6$): δ=11.30 (s, 1H, C(O)CHC(NH)), 5.15 (s, 1H, C(O)CHC(NH)), 2.80 (m, 2H, $HNCH_2CH_2N(CH_3)_2$), 2.05 (t, 2H, $HNCH_2CH_2N(CH_3)_2$), 1.95 (s, 6H, $N(CH_3)_2$), 1.50 (s, 3H, $C(NH)CH_3$), 1.35 (s, 9H, $C(CH_3)_3$).

EXAMPLE 2

Synthesis of 2,2-dimethyl-5-(diethylaminoethyl-imino)-3-hexanone

In a procedure analogously to 2,2-dimethyl-5-(dimethylaminoethyl-imino)-3-hexanone, starting with 2,2-dimethyl-hexa-3,5-dione (5.07 g, 36 mmol), $Na_2SO_4$ (3.5 g, 24.66 mmol), and 3-(diethylamino)ethylamine (5.25 g, 45 mmol). An orange/yellow liquid was obtained via a short-path vacuum distillation apparatus after removal of all volatiles. The yield is 78%.

$^1$H NMR (500 MHz, $C_6D_6$): δ=11.27 (s, 1H, C(O)CHC(NH)), 5.16 (s, 1H, C(O)CHC(NH)), 2.82 (m, 2H, $HNCH_2CH_2N(CH_2CH_3)_2$), 2.26 (q, 4H, $N(CH_2CH_3)_2$), 2.20 (t, 2H, $HNCH_2CH_2N(CH_2CH_3)_2$), 1.55 (s, 3H), 1.25 (s, 9H, $C(CH_3)_3$), 0.86 (t, 6H, $N(CH_2CH_3)_2$).

EXAMPLE 3

Synthesis of 2,2-dimethyl-5-(dimethylaminopropyl-imino)-3-hexanone

In a procedure analogously to 2,2-dimethyl-5-(dimethylaminoethyl-imino)-3-hexanone, starting with 2,2-dimethyl-hexa-3,5-dione (19.27 g, 136 mmol), $Na_2SO_4$ (13 g, 92 mmol), and 3-(dimethylamino)propylamine (15.72 g, 154 mmol). A yellow liquid was obtained via a short-path vacuum distillation apparatus after removal of all volatiles. The yield is 89%.

$^1$H NMR (500 MHz, $C_6D_6$): δ=11.30 (s, 1H, C(O)CHC(NH)), 5.17 (s, 1H, C(O)CHC(NH)), 2.84 (q, 2H, $HNCH_2CH_2N(CH_3)_2$), 2.05 (t, 2H, $HNCH_2CH_2CH_2N(CH_3)_2$), 1.94 (s, 6H, $N(CH_3)_2$), 1.54 (s, 3H, $C(NH)CH_3$), 1.32 (m, 2H, $HNCH_2CH_2CH_2N(CH_3)_2$), 1.27 (s, 9H, $C(CH_3)_3$).

EXAMPLE 4

Synthesis of 2,2-dimethyl-5-(diethylaminopropyl-imino)-3-hexanone

In a procedure analogously to 2,2-dimethyl-5-(dimethylaminoethyl-imino)-3-hexanone, starting with starting with 2,2-dimethylhexa-3,5-dione (3.50 g, 25 mmol), $Na_2SO_4$ (4.81 g, 34 mmol), and 3-(dimethylamino)propylamine (3.57 g, 27 mmol). The resulting light yellow/green liquid was vacuum distilled via a short-path apparatus to provide a yield of 67%.

$^1$H NMR (500 MHz, $C_6D_6$): δ=11.41 (s, 1H, C(O)CHC(NH)), 5.17 (s, 1H, C(O)CHC(NH)), 2.84 (q, 2H, $HNCH_2CH_2N(CH_3)_2$), 2.28 (q, 4H, $N(CH_2CH_3)_2$), 2.19 (t, 2H, $HNCH_2CH_2CH_2N(CH_2CH_3)_2$), 1.53 (s, 3H, $C(NH)CH_3$), 1.33 (m, 2H, $HNCH_2CH_2CH_2N(CH_2CH_3)_2$), 1.28 (s, 9H, $C(CH_3)_3$), 0.86 (t, 6H, $N(CH_2CH_3)_2$).

EXAMPLE 5

Synthesis of 4-(dimethylaminoethyl-imino)-2-pentanone

In a procedure analogously to 2,2-dimethyl-5-(dimethylaminoethyl-imino)-3-hexanone, starting with starting with 2,4-pentadione (8.00 g, 80.7 mmol), $Na_2SO_4$ (14 g, 98.64 mmol), and 3-(dimethylamino)ethylamine (7.83 g, 88.8 mmol). A green liquid was obtained via vacuum distillation at an oil bath of 95-105° C. under 150 mTorr. The yield was 83%. GC analysis indicated one peak.

$^1$H NMR (500 MHz, $C_6D_6$): δ=11.11(br, s, 1H, C(O)CHC(NH)), 4.88 (s, 1H, C(O)CHC(NH)), 2.78 (m, 2H, $HNCH_2CH_2N(CH_3)_2$), 2.01 (t, 3H, $HNCH_2CH_2N(CH_3)_2$), 2.00 (s, 3H, $C(O)CH_3$), 1.93 (s, 6H, $N(CH_3)_2$), 1.47 (s, 3H, $C(NH)CH_3$).

EXAMPLE 6

Synthesis of bis(2,2-dimethyl-5-(dimethylaminoethyl-imino)-3-hexanonato-N,O,N')strontium 40.0 g (0.066 mol) of $Sr(N(SiMe_3)_2)_2$·2THF was loaded in a 500 mL Schlenk flask with 100 ml THF. To this flask was dropwise added 29.0 g (0.14 mol) wax-like 2,2-dimethyl-5-(dimethylaminoethyl-imino)-3-hexanone in 100 mL of THF. The resulting light yellow clear solution was stirred at room temperature over night. All volatiles were then removed under vacuum to give a yellow solid which was dissolved in 100 mL of hot hexanes. GC/MS analysis of the trapped volatile liquid indicated it contains THF and by-product hexamethylsilylamine. GC/MS of the yellow solid dissolving in THF revealed there is only 2,2-dimethyl-5-(dimethylamino-ethyl-imino)-3-hexanone besides THF, suggesting the solid contains the tridentate β-ketoiminate ligand. The hexanes solution was then concentrated to about 30 mL to precipitate white crystals on the bottom. The flask was kept at −20° C. to afford more colorless crystals. 26.1 g of the crystals was collected and dried under vacuum. The yield is 77% on the basis of strontium.

Elemental analysis: calcd for $C_{24}H_{46}N_4O_2Sr$: C, 56.49; N, 10.98; H, 9.09. Found: C, 56.34; N, 11.32; H, 8.91. $^1H$ NMR (500 MHz, $C_6D_6$): δ=5.16 (s, 2H), 2.97 (t, 4H), 2.26 (b, 4H), 1.89 (s, 12H), 1.77 (s, 6H), 1.37 (s, 18H).

Figure 2:
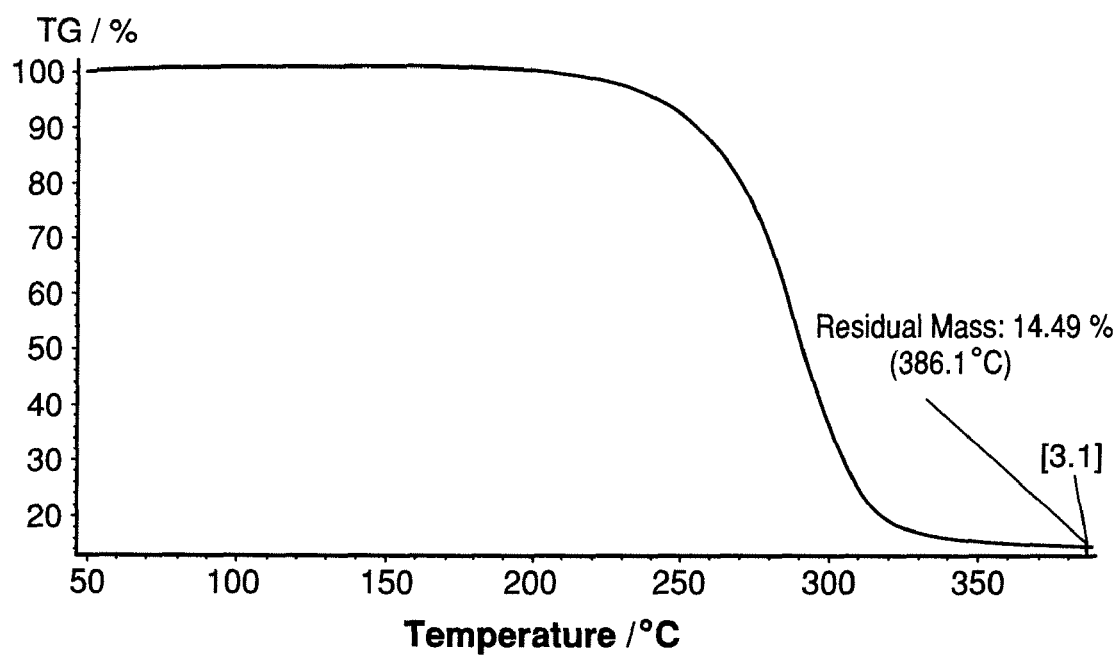
FIG. 2 is a TGA diagram of bis(2,2-dimethyl-5-(dimethylaminoethyl-imino)-3-hexanonato-N,O,N')strontium, indicating the complex is volatile but decomposes at higher temperature.

A colorless crystal of bis(2,2-dimethyl-5-((dimethylaminoethylene)imino)-3-hexanonato)strontium was structurally characterized by X-ray single crystal analysis (see FIG. 1). The structure below shows strontium is coordinated with two 2,2-dimethyl-5-(dimethylamino)ethylene)imino)-3-hexanonato ligands in a distorted octahedral environment. The Sr—N distances range from 2.614 to 2.690 Å and the average Sr—O is 2.353 Å. FIG. 2 exhibits a TGA diagram of bis(2,2-dimethyl-5-(dimethylaminoethyl-imino)-3-hexanonato-N,O,N') strontium, indicating the complex is volatile but decomposes at higher temperature.

EXAMPLE 7

Synthesis of bis(2,2-dimethyl-5-(diethylaminoethyl-imino)-3-hexanonato-N,O,N')strontium In a procedure analogously to example 6, starting with $Sr(N(SiMe_3)_2)_2 \cdot 2THF$ (2.66 g, 0.005 mol) and 2,2-dimethyl-5-(diethylaminoethyl-imino)-3-hexanone (2.0 g, 0.008 mol). 1.91 g of the crystals was collected and dried under vacuum after removal of all volatiles and work-up. The yield is 84% on the basis of strontium.

Elemental analysis: calcd for $C_{28}H_{54}N_4O_2Sr$: C, 59.38; N, 9.89; H, 9.61. Found: C, 58.99; N, 9.90; H, 9.51. $^1H$ NMR (500 MHz, $C_6D_6$): δ=5.14 (s, 2H), 2.11 (t, 4H), 2.67 (b, 4H), 2.54 (b, 8), 1.76 (s, 6H), 1.36 (s, 18H), 0.74 (t, 12H).

A colorless crystal of bis(2,2-dimethyl-5-(diethylaminoethyl-imino)-3-hexanonato)strontium was structurally characterized by X-ray single crystal analysis. The structure below shows strontium is coordinated with two 2,2-dimethyl-5-(diethylaminoethyl-imino)-3-hexanonato ligands in a distorted octahedral environment. The Sr—N distances range from 2.604 to 2.677 Å and the average Sr—O is 2.374 Å.

EXAMPLE 8

Synthesis of tris(2,2-dimethyl-5-(dimethylaminoethyl-imino)-3-hexanonato)yttrium In a procedure analogously to example 6, starting with $Y(N(SiMe_3)_2)_3$ (2.00 g, 3.9 mmol)) and 2,2-dimethyl-5-(dimethylaminoethyl-imino)-3-hexanone (2.41 g, 11.35 mmol). 1.57 g of white solid was collected and the yield is 57% on the basis of yttrium.

Elemental analysis: calcd for $C_{36}H_{69}N_6O_3Y$: C, 59.81; N, 9.63; H, 11.63. Found: C, 59.81; N, 9.37; H, 11.83. $^1H$ NMR (500 MHz, $C_6D_6$): δ=5.14 (s, 3H), 3.47 (t, 6H), 2.49 (t, 6H), 2.22 (s, 18H), 1.81 (s, 9H), 1.27 (s, 27H).

Figure 3:
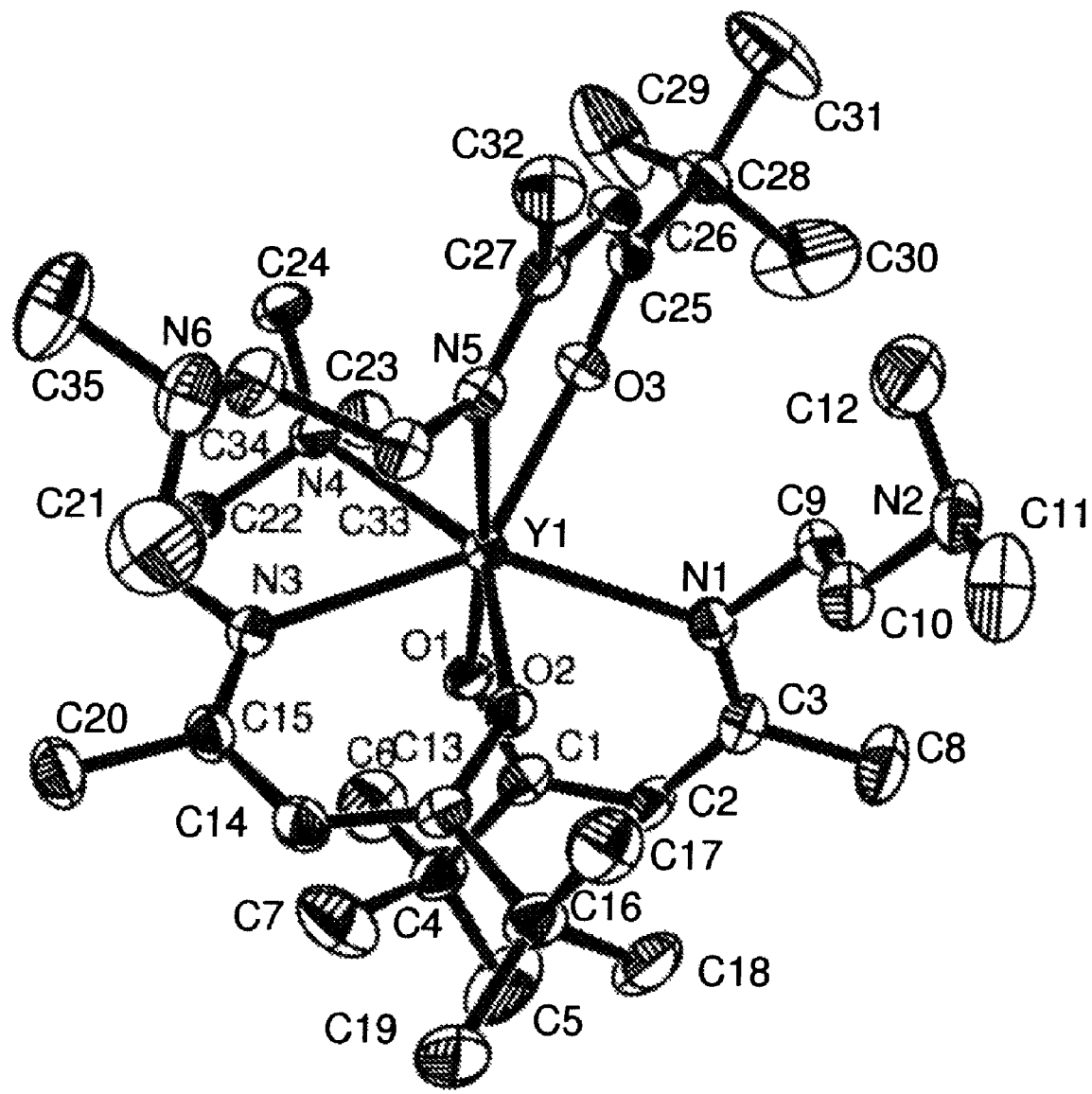
FIG. 3 is a drawing representing the crystal structure of tris(2,2-dimethyl-5-(dimethylaminoethyl-imino)-3-hexanonato)ytterium.

A colorless crystal of tris(2,2-dimethyl-5-(dimethylaminoethyl-imino)-3-hexanonato)yttrium was structurally characterized by X-ray single crystal analysis (see FIG. 3), revealing that the yttrium atom is coordinated with three 2,2-dimethyl-5-(dimethylaminoethyl-imino)-3-hexanonato ligands.

EXAMPLE 9

Synthesis of bis(2,2-dimethyl-5-(dimethylaminoethyl-imino)-3-hexanonato)cobalt

Procedures (a) and (b) are shown for producing this compound. (a) 2 g (0.015 mol) of anhydrous $CoCl_2$ was loaded in a 500 mL Schlenk flask with 30 ml THF. To this flask was added (2,2-dimethyl-5-(dimethylaminoethyl-imino)-3-hexanonato)Li prepared in situ by the reaction of 2,2-dimethyl-5-(dimethylaminoethyl-imino)-3-hexanone (6.4 g, 0.03 mol) with a 2.5 M $LiBu^n$ hexane solution (12 mL, 0.03 mol) in 40 mL of hexanes at −78° and stirred at room temperature for 30 min. The mixture was stirred at room temperature over night. After the reaction was complete, all volatiles were then removed under vacuum to give rise to a dark brown solid. Extraction and filtration produced a dark brown solution and brown solid. The brown was LiCl contaminated with trace amount of Co compounds. The brown solution was then dried at 50° C. to yield a dark brown solid. Sublimation of the dark brown solid at 105° C. and 50 Torr provide greenish brown microcrystals. The yield is 50% on the basis of cobalt.

Elemental Analysis for $CoC_{24}H_{46}N_4O_2$: C, 59.86; N, 11.63; H, 9.63. Found: C, 59.73; N, 11.62; H, 9.77. $^1H$ NMR (500 MHz, $C_6D_6$): δ=119.04, 25.38, 11.86, 3.42, 1.36, 0.43, −16.00, −97.00.

Figure 4:
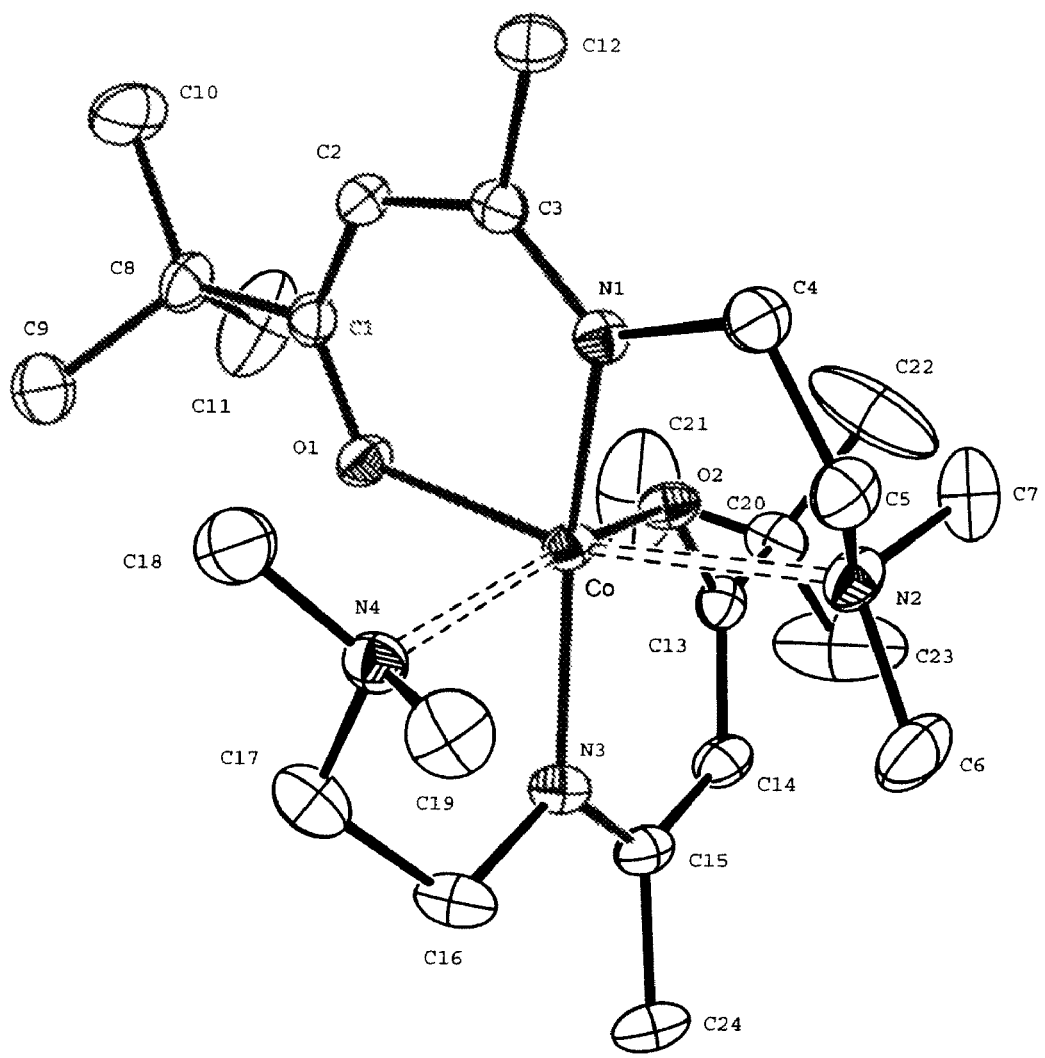
FIG. 4 is a drawing representative of the crystal structure of bis(2,2-dimethyl-5-(dimethylaminoethyl-imino)-3-hexanonato)cobalt.

Procedure (b) A single crystal of bis(2,2-dimethyl-5-(dimethylaminoethyl-imino)-3-hexanonato) cobalt was characterized by X-ray single crystal analysis (see FIG. 4), exhibiting that the cobalt atom is coordinated with two 2,2-dimethyl-5-(diethylaminoethyl-imino)-3-hexanonato ligands in a distorted octahedral environment.

(b). NaH (0.34 g, 14 mmol) was slowly added to a solution of 2,2-dimethyl-5-(diethylaminoethyl-imino)-3-hexanone (2.07 g, 12 mmol) in 70 mL of THF. After bubbling ceased, $CoCl_2$ (1.07 g, 8 mmol) was added to reaction flask. 2.25 g of brown crystals were collected after workup and the yield was 69%.

EXAMPLE 10

Synthesis of bis(2,2-dimethyl-5-(dimethylaminopropyl-imino)-3-hexanonato)cobalt

In a procedure similar to example 9, starting with 2,2-dimethyl-5-(dimethylaminopropylene-imino)-3-hexanone (1.50 g, 0.007 mol) and (0.22 g, 0.009 mol) NaH (0.22 g, 0.009 mol), $CoCl_2$ (0.38 g, 0.003 mol) was added. Following workup, the orange crystals were obtained by sublimation of the resulting brown solid. The yield is 82%.

Elemental Analysis for $CoC_{26}H_{50}N_4O_2$: C, 61.27; N, 10.99; H, 9.89. Found: C, 61.42; N, 11.19; H, 9.43. $^1H$ NMR (500 MHz, $C_6D_6$): δ=14.40, 8.83, 1.42, −1.45, −5.54, −21.49, −31.91.

A single crystal of bis(2,2-dimethyl-5-(dimethylaminopropyl-imino)-3-hexanonato) cobalt was characterized by X-ray single crystal analysis, exhibiting that the cobalt atom is coordinated with two 2,2-dimethyl-5-(dimethylaminopropyl-imino)-3-hexanonato ligands in an octahedral environment.

EXAMPLE 11

Synthesis of bis(4-(dimethylaminoethyl-imino)-2pentanonato)cobalt

In a procedure similar to example 9, starting with (2.07 g, 0.012 mol) 4-(dimethylaminoethyl-imino)-2-hexenone (2.07 g, 0.012 mol) and (0.34 g, 0.14 mol) NaH, followed by addition of $CoCl_2$ (1.07 g, 0.008 mol) was added. Crystals were grown from a hexane solution and the yield is 69%.

Elemental Analysis for CoC$_{18}$H$_{34}$N$_4$O$_2$: C, 54.40; N, 14.83; H, 8.62. Found: C, 54.72; N, 14.04; H, 10.10. $^1$H NMR (500 MHz, C$_6$D$_6$): δ=25.47, 17.44, 8.69, 1.35, −9.47, −12.00, −21.40, −116.00, 120.04.

EXAMPLE 12

Synthesis of bis(2,2-dimethyl-5-(dimethylaminoethyl-imino)-3-hexanonato)nickel

In a procedure similar to example 9, starting with (3.48 g, 0.016 mol) 2,2-dimethyl-5-(dimethylaminoethyl-imino)-3-hexanone (3.48 g, 0.016 mol) and 2.5M butyl lithium (6.5 mL, 0.016 mol), followed by addition of NiCl$_2$ (1.02 g, 0.008 mol) was added. Upon sublimation the bright green solid was obtained with a yield of 66%.

Elemental Analysis for NiC$_{24}$H$_{46}$N$_4$O$_2$: C, 59.89; N, 11.63; H, 9.63. Found: C, 60.80; N, 11.62; H, 8.80.

Figure 5:
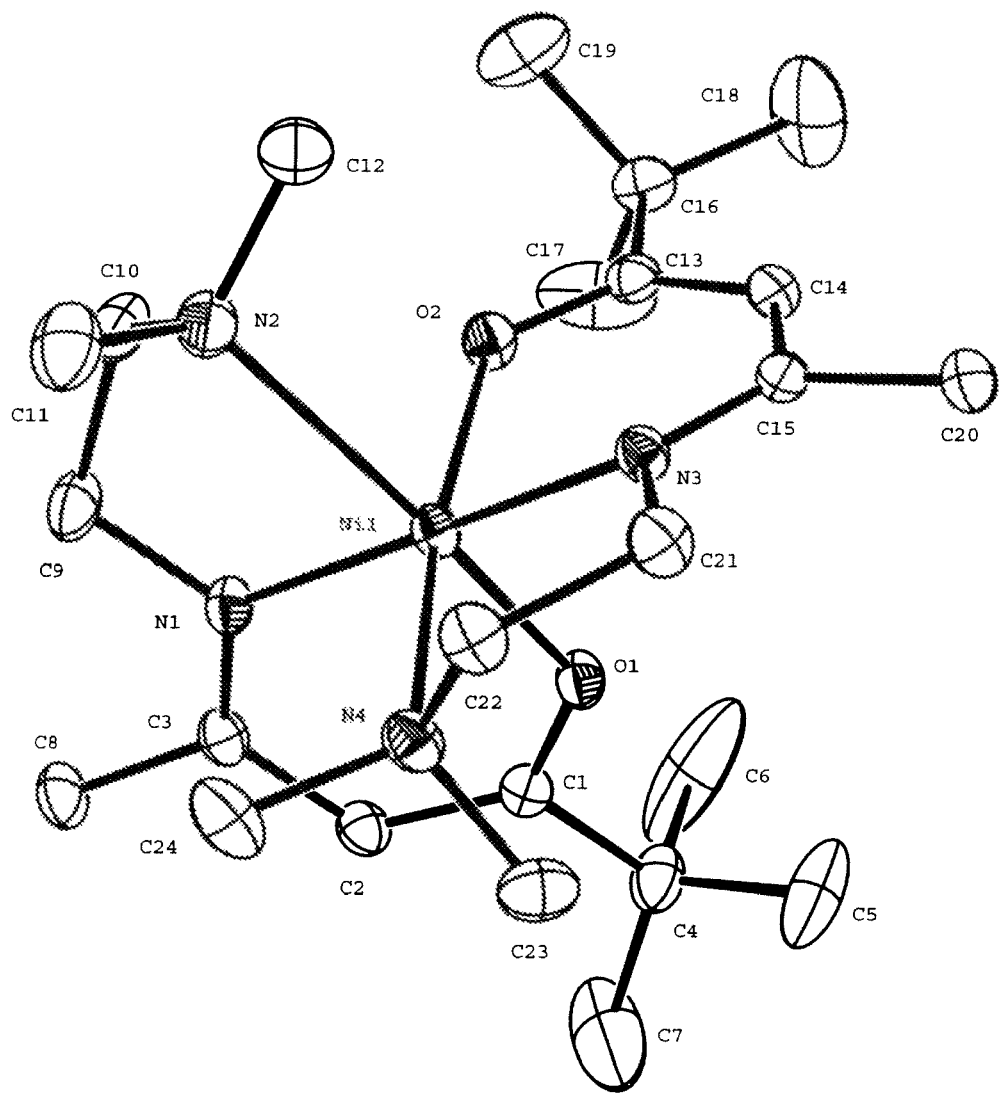
FIG. 5 is a drawing representative of the crystal structure of bis(2,2-dimethyl-5-(dimethylaminoethyl-imino)-3-hexanonato)nickel.

A single crystal of bis(2,2-dimethyl-5-(dimethylaminoethyl-imino)-3-hexanonato) nickel was characterized by X-ray single crystal analysis (see FIG. 5), exhibiting that the nickel atom is coordinated with two 2,2-dimethyl-5-(dimethylaminoethyl-imino)-3-hexanonato ligands in an octahedral environment.

EXAMPLE 13

Synthesis of bis(2,2-dimethyl-5-(dimethylaminopropyl-imino)-3-hexanonato)nickel

In a procedure similar to example 9, starting with 2,2-dimethyl-5-(dimethylaminopropyl-imino)-3-hexanone (3.66 g, 0.016 mol) and 2.5M butyl lithium (6.3 mL, 0.015 mol) followed by addition of NiCl$_2$ (1.01 g, 0.008 mol) was added. Green crystals were harvested from hexane solution.

Elemental Analysis for NiC$_{26}$H$_{50}$N$_4$O$_2$: C, 61.30; N, 11.52; H, 9.89. Found: C, 61.52; N, 11.06; H, 9.34. $^1$H NMR (500 MHz, C$_6$D$_6$): δ=60.00, 36.56, 3.57, 1.47, −2.84, 14.70, 16.10, −76.00.

A single crystal of bis(2,2-dimethyl-5-(dimethylaminopropyl-imino)-3-hexanonato) nickel was characterized by X-ray single crystal analysis, exhibiting that the nickel atom is coordinated with two (2,2-dimethyl-5-(dimethylaminopropyl-imino)-3-hexanonato) ligands in an octahedral environment.

EXAMPLE 14

Synthesis of bis(4-(dimethylaminoethyl-imino)-2-pentanonato)nickel

In a procedure similar to Example 9, starting with 4-(dimethylaminoethyl-imino)-2-hexanone (2.15 g, 0.013 mol) and NaH (0.36 g, 0.015 mol), and NiCl$_2$ (0.74 g, 0.006 mol) was added. The product was sublimed and crystallized from hexane. Yield is 74%.

Elemental Analysis for NiC$_{18}$H$_{34}$N$_4$O$_2$: C, 54.43; N, 14.10; H, 8.63. Found: C, 54.21; N, 14.04; H, 10.10.

EXAMPLE 15

Synthesis of tris(isopropoxy)(2,2-dimethyl-5-(dimethylaminoethyl-imino)-3-hexanonato)titanium(IV)

Ti (OCH(CH3)2)4(2.00 g, 0.007 mol), (1.45 g, 0.007 mol) 2,2-dimethyl-5-(dimethylaminoethyl-imino)-3-hexanone (1.45 g, 0.007 mol), and 15 mL hexane were loaded into a 100 mL Schlenk flask. The mixture was stirred at 40° C. for 16 hours. Under vacuum all volatiles were removed, and the yellow powdery solid was washed with hexane and dried. Sublimation provides the light green crystals with a yield of 90%.

$^1$H NMR (500 MHz, C$_6$D$_6$): δ=5.18 (s, 1H), s, 1H), 5.00 (b, 3H), 2.96 (s, 2H), 2.48 (s, 6H), 2.28 (t, 2H), 1.53 (s, 3H), 1.35 (s, 9H), 1.30 (s, 18H).

EXAMPLE 16

Synthesis of tris(isopropoxy)(4-(dimethylaminoethyl-imino)-2-pentanonato)titanium In a procedure similar to Example 15, stirring (2.08 g, 0.007 mol) Ti (OCH(CH$_3$)$_2$)$_4$ and (1.19 g, 0.007 mol) 5-(dimethylaminoethyl-imino)-3-hexanonato. Sublimation of the sticky yellow solid produced light green crystals, yielding 74%.

Elemental Analysis for C$_{18}$H$_{38}$N$_2$O$_4$Ti: C, 54.82; N, 9.71; H, 7.10. Found: C, 52.50; N, 9.50; H, 7.39. $^1$H NMR (500 MHz, C$_6$D$_6$): δ=4.92 (b, 3H) 4.83 (s, 1H), 2.96 (s, 2H), 2.47(s, 6H), 2.27 (t, 2H), 1.95 (s, 3H), 1.45 (s, 6H), 1.30 (s, 18H).

A single crystal of tris(isopropoxy)(4-(dimethylaminoethyl-imino)-3-hexanonato)titanium was characterized by X-ray single crystal analysis, exhibiting that the Titanium atom was coordinated with three isopropoxy groups and one 5-(dimethylaminoethyl-imino)-3-hexanonato ligand.

EXAMPLE 17

Synthesis of tris(tert-butoxy)(4-(dimethylaminoethyl-imino)-2-pentanonato)hafnium(IV)

In a procedure similar to Example 15, starting with Hf(OC (CH$_3$)$_3$)$_4$ (2.73 g, 0.006 mol) and 5-(dimethylaminoethyl-imino)-3-hexanone (1.01 g, 0.005 mol). Volatiles were examined via GC/MS, and 2-methyl-2-propanol was observed. The white solid was collected with a yield of 95%. Crystallization from pentane/hexane solution provides colorless block-like crystals.

$^1$H NMR (500 MHz, C$_6$D$_6$): δ=4.81 (s, 1H), 2.89 (t, 2H), 2.44 (s, 8H), 1.55 (s, 9H), 1.42 (s, 3H), 1.36 (s, 18H)

EXAMPLE 18

Synthesis of tris(tert-butoxy)(2,2-dimethyl-5-(dimethylaminoethyl-imino)-3-hexanonato)zirconium (IV)

In a procedure similar to Example 15, starting with Zr(OC (CH$_3$)$_3$)$_4$ (1.81 g, 0.005 mol) and 2,2-dimethyl-5-(dimethylaminoethyl-imino)-3-hexanone ((1.05 g, 0.005 mol). Workup provided a light yellow solid with a yield of 95%.

$^1$H NMR (500 MHz, C$_6$D$_6$): δ=4.86 (s, 1H, BuCOCHCN), 2.91 (b, t, 2H, NCH$_2$CH$_2$NMe$_2$), 2.39 (b, s, 6H, CH$_2$N(CH$_3$)$_2$), 2.39 (b, t, 2H, NCH$_2$CH$_2$NMe$_2$), 1.55 (s, 9H, (CH$_3$)$_3$CCO), 1.49 (s, 3H, COCHCN(CH$_3$)), 1.31 (s, 27H, (OC (CH$_3$)$_3$)

A colorless crystal of tris(tert-butoxy)(2,2-dimethyl-5-(dimethylaminoethyl-imino)-3-hexanonato)zirconium(IV) was characterized by X-ray single crystal analysis, exhibiting that the zirconium atom was coordinated with three tert-butoxy groups and one substituted 2,2-dimethyl-5-(dimethylaminoethyl-imino)-3-hexanonato ligand.

EXAMPLE 19

Synthesis of tris(tert-butoxy)(4-(dimethylaminoethyl-imino)-2-pentanonato)zirconium(IV)

In a procedure similar to Example 15, stirring (2.2 g, 0.006 mol) $Zr(OC(CH_3)_3)_4$ (2.2 g, 0.006 mol) and 5-(dimethylaminoethyl-imino)-3-hexanone (1.0 g, 0.006 mol) in THF produced a light yellow solid with a yield of 82% upon workup.
$^1$H NMR (500 MHz, $C_6D_6$): δ=4.86 (s, 1H, $CH_3COCHCN$), 2.90 (s, 2H, $NCH_2CH_2NMe_2$), 2.36 (b, s, 6H, $CH_2N(CH_3)_2$), 2.36 (b, t, 2H, $NCH_2CH_2NMe_2$), 1.89 (s, 3H, $CH_3COCHCN$), 1.51 (s, 9H, $CH_3(CH_3)_2)COCH$), 1.41 (s, 3H, $CH_3COCHCNCH_3$), 1.35 (s, 18H, $(CH_3)_2(CH_3)COCH$)

Figure 6:
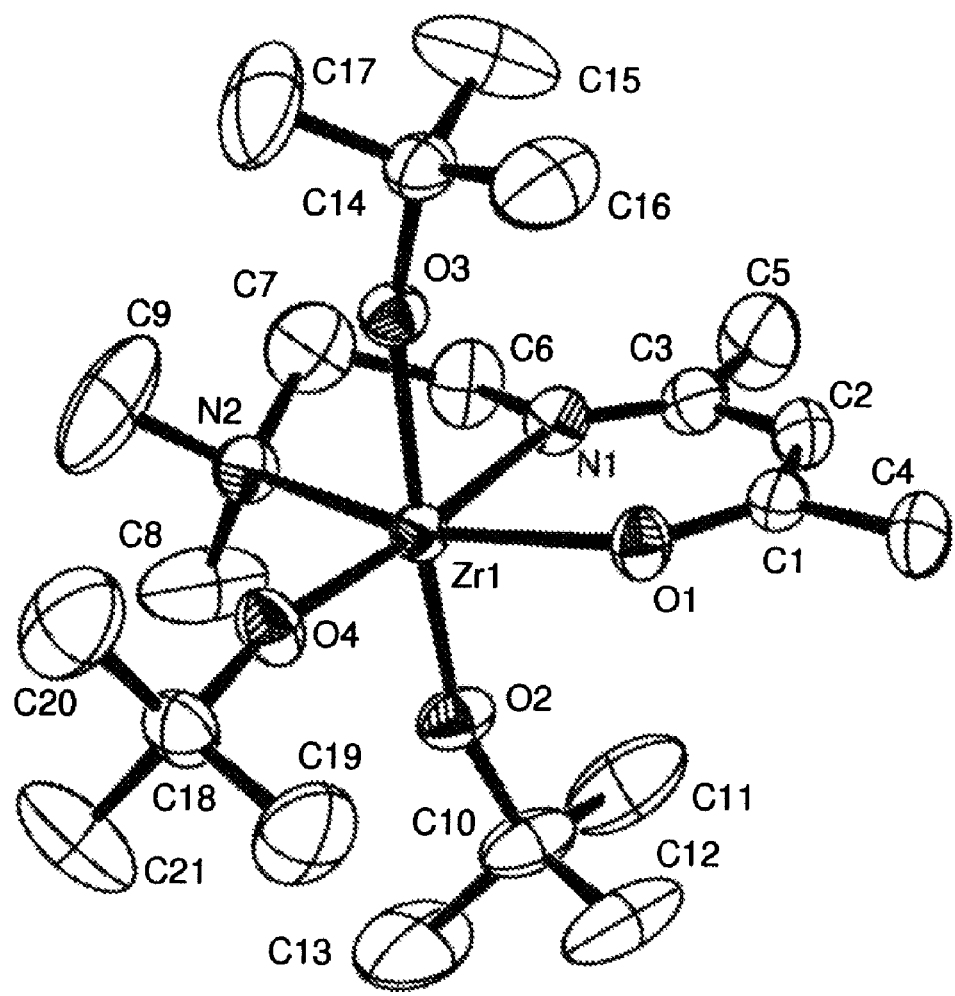
FIG. 6 is a drawing representative of the crystal structure of tris(tert-butoxy( )(4-(dimethylaminoethyl-imino)-2-hexanonato)zirconium(IV).
Figure 7:
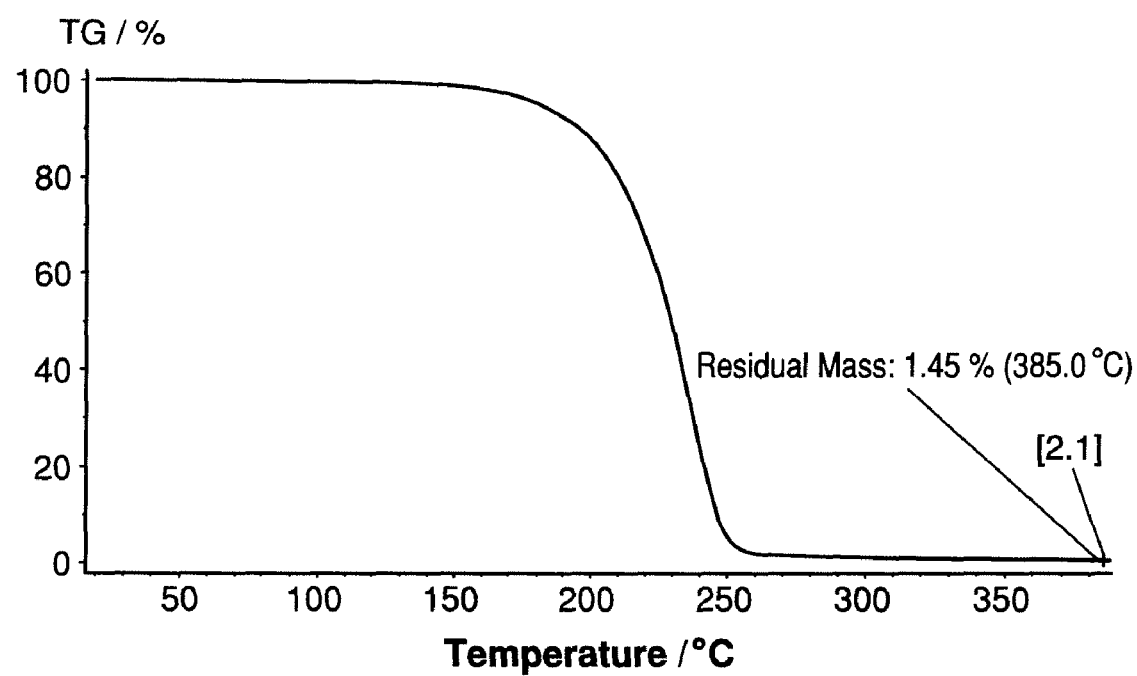
FIG. 7 is a TGA diagram of tris(tert-butoxy)(4-(dimethylaminoethyl-imino)-2-hexanonato)zirconium(IV), indicating the complex is volatile with less than 2% residue.
Figure 8:
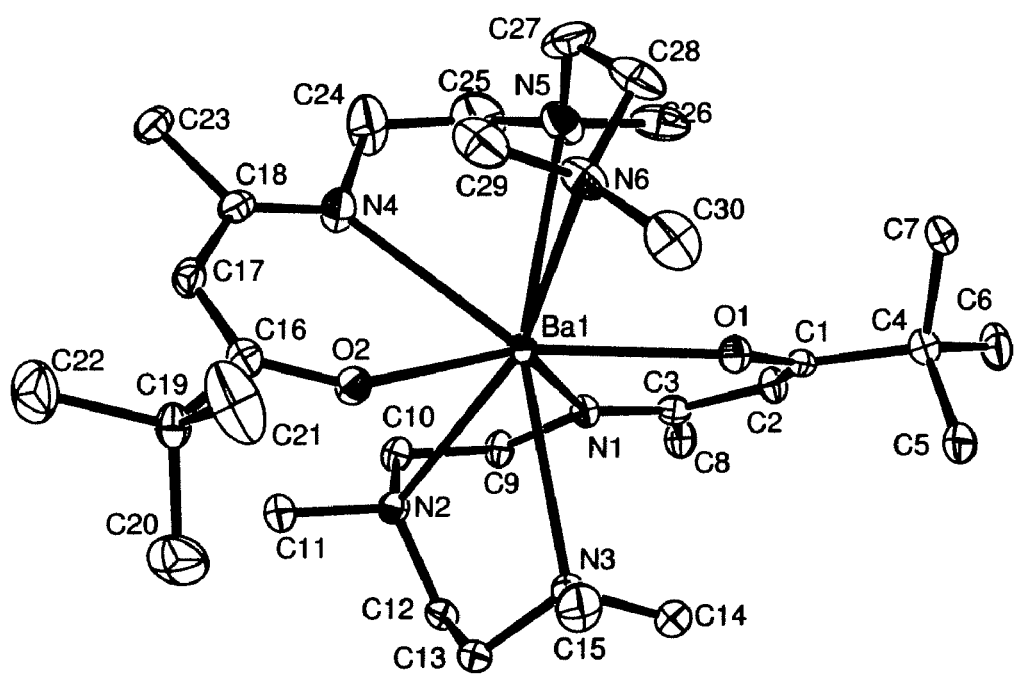
FIG. 8 is a drawing representing the crystal structure of bis(2,2-dimethyl-5-(2-(2-(dimethylamino-ethyl)(methylamino))ethyl-imino)-3-hexanonato)barium.

A colorless crystal of tris(tert-butoxy( )(4-(dimethylaminoethyl-imino)-2-hexanonato)zirconium(IV) was characterized by X-ray single crystal analysis (see FIG. 6), exhibiting that the zirconium atom was coordinated with three tert-butoxy groups and one substituted 4-(dimethylaminoethyl-imino)-2-hexanonato ligand. FIG. 7 reveals that a TGA diagram of tris(tert-butoxy)(4-(dimethylaminoethyl-imino)-2-hexanonato)zirconium(IV), indicating the complex is volatile with less than 2% residue.

EXAMPLE 20

Synthesis of bis(2,2-dimethyl-5-(dimethylaminoethyl-imino)-3-hexanonato)barium

In a procedure analogously to example 6, starting with $Ba(N(SiMe_3)_2)_2 \cdot 2THF$ and 2,2-dimethyl-5-(diethylaminoethyl-imino)-3-hexanone. A very viscous orange oil was obtained upon removal of all volatiles. NMR indicates there are some unreacted 2,2-dimethyl-5-(diethylaminoethyl-imino)-3-hexanone. The free ligand was removed via a short-path distillation to provide an orange solid.
$^1$H NMR (500 MHz, $C_6D_6$): δ=5.11 (br, s), 3.10 (br, s), 2.21 (br, s), 1.95 (br, s), 1.80 (s, 6H), 1.38 (s).

EXAMPLE 21

Synthesis of tetrakis(ethoxy)(4-(dimethylaminoethyl-imino)-2-pentanonato)tantalum(V)

2,2-dimethyl-(5-(dimethylamino)propyl-imino)-3-hexenone (0.64 g, 3.8 mmol) was slowly added a flask Loaded with $Ta_2(OEt)_{10}$ (1.50 g, 1.85 mmol) to added. The flask was heated to 80° C. for 3 hours and then the by-product ethanol was removed under vacuum to yield 1.6 g of clear orange liquid. The yield is 1.6 g, 98%.
$^1$H NMR (500 MHz, $C_6D_6$): δ=4.79 (s, 1H), 4.76 (q, 2H), 4.71 (q, 2H), 4.31 (q, 2H), 4.28 (q, 2H), 3.74 (t, 2H), 2.60 (t, 2H), 2.13 (s, 6H), 1.85 (s, 3H), 1.70 (s, 3H), 1.40 (t, 3H), 1.38 (t, 3H), 1.20 (t, 6H).

EXAMPLE 22

Synthesis of 2,2-dimethyl-5-(2-(2-(dimethylamino)ethoxy)ethyl-imino)-3-hexanone

In a 100 mL round bottom flask equipped with a magnetic stirrer, 8 g 2,2-dimethylhexane-3,5-dione was combined with 1.1 equivalents of 2-(2-(dimethylamino)ethoxy)ethylamine, anhydrous sodium sulfate and anhydrous diethyl ether and stirred over three days under nitrogen. The ether was removed on a rotary evaporator and the residue was vacuum distilled through a Vigreux column to yield 9.7 g of product.
$^1$H NMR: (300 MHz, $THF_{d8}$): δ=11.05 (s, 1H), 5.06 (s, 1H), 3.51 (t, 2H), 3.50 (t, 2H), 3.37 (q, 2H), 2.42 (t, 2H), 2.17 (s, 6H), 1.92 (s, 3H), 1.05 (s, 9H).

EXAMPLE 23

Synthesis of bis(2,2-dimethyl-5-(2-(2-(dimethylamino)ethoxy)ethyl-imino)-3-hexanonato)barium In a 100 mL Schlenk flask with magnetic stirrer, in a glove box, 1.25 g sublimed barium metal was combined with 3.15 g 2,2-dimethyl-5-(2-(2-(dimethylamino)ethoxy)ethyl-imino)-3-hexanone and 30 mL anhydrous THF. The flask was placed on a Schlenk line and fitted with a cold finger condenser. Anhydrous ammonia was allowed to condense into the flask and refluxed with the cold finger condenser for 4 hours. The flask and condenser were allowed to warm up to room temperature over night and the ammonia was allowed to escape through a gas bubbler. The cloudy amber solution was filtered through celite and the product was crystallized from hot hexanes as white crystals.
$^1$H NMR: (300 MHz, $THF_{d8}$): δ=4.64 (s, 1H), 3.94 (t, 2H), 3.71 (t, 2H), 3.51 (t, 2H), 2.49 (t, 2H), 2.18 (s, 6H), 1.78 (s, 3H), 1.10 (s, 9H).

EXAMPLE 24

Synthesis of 2,2-dimethyl-5-(2-(2-(dimethylaminoethyl)(methylamino))ethyl-imino)-3-hexanone In a 100 mL round bottom flask equipped with a magnetic stirrer, 1.9 g 2,2-dimethylhexane-3,5-dione was combined with 1.1 equivalents of 2-(2-(dimethylamino-ethyl)(methylamino))ethylamine, anhydrous sodium sulfate and anhydrous diethyl ether and stirred over night under nitrogen. The ether was removed on a rotary evaporator and the residue was vacuum distilled through a Vigreux column to yield 2.7 g of product.
$^1$H NMR: (300 MHz, $THF_{d8}$): δ=10.99 (s, 1H), 5.06 (s, 1H), 3.28 (Q, 2H), 2.53 (t, 2H), 2.48 (t, 2H), 2.37 (t, 2H), 2.25 (s, 3H), 2.15 (s, 6H), 1.92 (s, 3H), 1.06 (s, 9H).

EXAMPLE 25

Synthesis of bis(2,2-dimethyl-5-(2-(2-(dimethylamino-ethyl)(methylamino))ethyl-imino)-3-hexanonato)barium In a 50 mL Schlenk flask with magnetic stirrer, in a glove box, 1.05 g sublimed barium metal was combined with 2.72 g 2,2-dimethyl-5-(2-(2-(dimethylamino -ethyl)(methylamino))ethyl-imino)-3-hexanone and 20 mL anhydrous THF. The flask was placed on a Schlenk line and fitted with a cold finger condenser. Anhydrous ammonia was allowed to condense into the flask and refluxed with the cold finger condenser for 4 hours. The flask and condenser were allowed to warm up to room temperature over night and the ammonia was allowed to escape through a gas bubbler. The cloudy grayish suspension was concentrated, suspended in hot hexanes and filtered through celite. The product was recrystallized from hot hexanes several times to give 0.4 g product as colorless crystals.

Elemental analysis: calcd for $C_{30}H_{60}BaN_6O_2$: C, 53.45; N, 12.47; H, 8.97. Found: C, 53.33; N, 12.71; H, 9.44. $^1$H NMR (500 MHz, C$_6$D$_6$): δ=5.07(s, 1H), 3.28 (br, s, 2H), 2.49 (very br, 6H), 2.23 (s, 6H), 2.22 (sh, 3H), 1.84 (s, 3H), 1.40 (s, 9H).

A single crystal of bis(2,2-dimethyl-5-(2-(2-(dimethylamino -ethyl)(methylamino))ethyl-imino)-3-hexanonato) barium was characterized by X-ray single crystal analysis, exhibiting that the barium atom is coordinated with two 2,2-dimethyl-5-(2-(2-(dimethylamino-ethyl)(methylamino)) ethyl-imino)-3-hexanonato ligands in tetradentate fashion.

EXAMPLE 26

Figure 9:
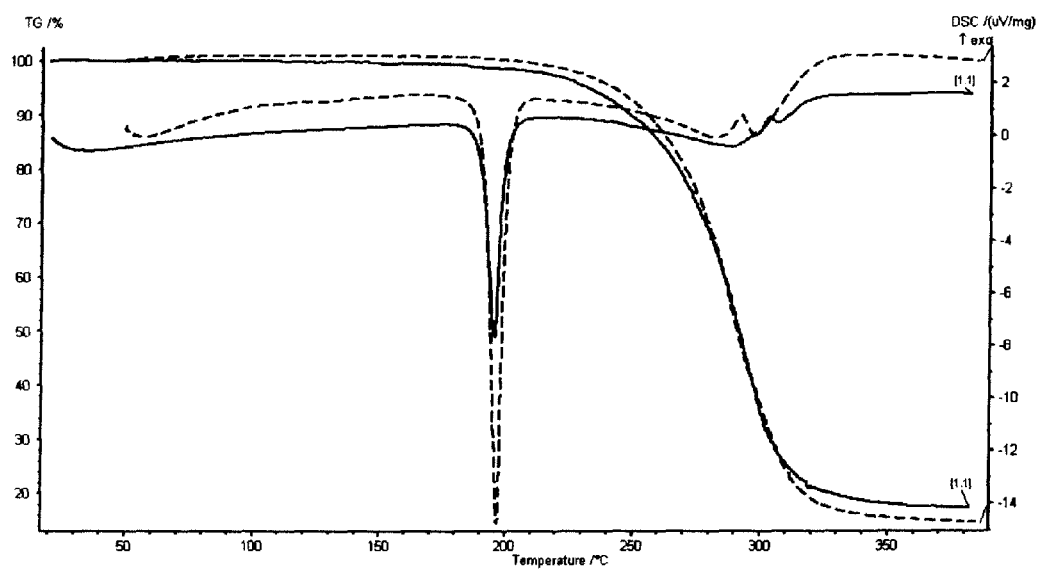
FIG. 9 is a TGA/DSC diagram of the TGA/DSC of bis(2, 2-dimethyl-5-(dimethylaminoethyl-imino)-3-hexanonato-N, O,N')strontium before (dashed line) and after (solid line) dissolving in NMP, suggesting that bis(2,2-dimethyl-5-(dimethylaminoethyl-imino)-3-hexanonato-N,O,N')strontium and NMP are compatible.

Preparation of 1M Solution of bis(2,2-dimethyl-5-(dimethylaminoethyl-imino)-3-hexanonato-N,O,N') strontium in N-methyl-2-pyrrolidinone To 1 ml vial containing 0.25 g of bis(2,2-dimethyl-5-(dimethylaminoethyl-imino)-3-hexanonato-N,O,N')strontium, 0.49 ml of N-methyl-2-pyrrolidinone (NMP) was added to result in a pale yellow clear solution. The solution was kept at room temperature over night and then dried under vacuum to give a pale yellow solid. FIG. 9 shows the TGA/DSC of bis(2,2-dimethyl-5-(dimethylaminoethyl-imino)-3-hexanonato-N,O,N')strontium before and after dissolving in NMP, suggesting that bis(2,2-dimethyl-5-(dimethylaminoethyl-imino)-3-hexanonato-N,O,N')strontium and NMP are compatible and the resulting solution can be used in CVD or ALD processes.

EXAMPLE 27

Preparation of 1.0M Solution of bis(2,2-dimethyl-5-(dimethylaminoethyl-imino)-3-hexanonato-N,O,N') strontium in N-cyclohexyl-2-pyrrolidinone 0.19 mL N-cyclohexyl-2-pyrrolidinone was added to a 2 mL vial containing bis(2,2-dimethyl-5-(dimethylaminoethyl-imino)-3-hexanonato-N,O,N')strontium (0.10 g, 0.20 mmol) to result in a light green clear solution. TGA of the solution indicates the mixture is volatile.

EXAMPLE 28

Preparation of 0.9M Solution of tris(isopropoxy)(4-(dimethylaminoethyl-imino)-2-hexenonato)titanium in N-methyl-2-pyrrolidinone 0.27 mL N-methyl-2-pyrrolidinone was added to a 2 mL vial containing tris(isopropoxy)(4-(dimethylaminoethyl-imino)-2-hexenonato)titanium (0.1 g, 0.25 mmol) to result in a bright orange solution. TGA of the solution indicates the mixture is volatile.

EXAMPLE 29

Preparation of 0.75M Solution of tris(tert-butoxy )(4-(dimethylaminoethyl-imino)-2-hexanonato) zirconium(IV) in N-methyl-2-pyrrolidinone 0.28 mL N-methyl-2-pyrrolidinone was added to a 2 mL vial containing tris(tert-butoxy( )(4-(dimethylaminoethyl-imino)-2-hexanonato)zirconium(IV) (0.10 g, 0.21 mmol) to result in a greenish yellow solution. TGA of the solution indicates the mixture is volatile.

The invention claimed is:

1. A metal containing complex represented by the structures selected from the group consisting of:

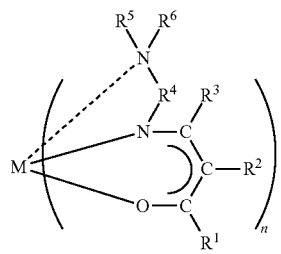

A wherein M is a metal group having a valence of from 2 to 5; $R^1$ is selected from the group consisting of alkyl, fluoroalkyl, cycloaliphatic, and aryl, having from 1 to 10 carbon atoms; $R^2$ is selected from the group consisting of hydrogen, alkyl, alkoxy, cycloaliphatic, and aryl; $R^3$ is selected from the group consisting of alkyl, fluoroalkyl, cycloaliphatic, and aryl; $R^4$ is an alkylene bridge; $R^{5-6}$ are individually selected from the group consisting of alkyl, fluoroalkyl, cycloaliphatic, aryl, and heterocyclic containing either oxygen, or nitrogen atoms; and n is an integer equal to the valence of the metal M;

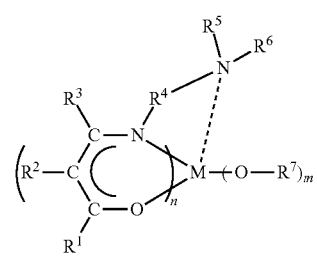

B wherein M is a metal ion selected from Group 4 and 5 metals; $R^1$ is selected from the group consisting of alkyl, fluoroalkyl, cycloaliphatic, and aryl, having from 1 to 10 carbon atoms; $R^2$ is selected from the group consisting of hydrogen, alkyl, alkoxy, cycloaliphatic, and aryl; $R^3$ is selected from the group consisting of alkyl, fluoroalkyl, cycloaliphatic, and aryl; $R^4$ is an alkylene bridge; $R^{5-6}$ are individually selected from the group consisting of alkyl, fluoroalkyl, cycloaliphatic, aryl, or heterocyclic containing an oxygen, or nitrogen atom; $R^7$ is selected from the group consisting of alkyl, fluoroalkyl, cycloaliphatic, and aryl; m and n are at least 1 and the sum of m plus n is equal to the valence of the metal M; and,

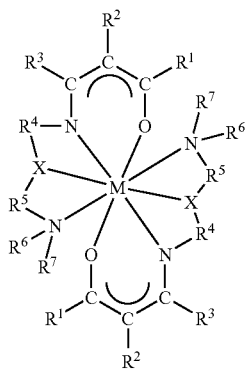

C wherein M is an alkaline earth metal; $R^1$ is selected from the group consisting of alkyl, fluoroalkyl, cycloaliphatic, and aryl, having from 1 to 10 carbon atoms; $R^{2-3}$ are individually selected from the group consisting of hydrogen, alkyl, alkoxy, cycloaliphatic, and aryl; $R^{4-5}$ are individually $C_{2-3}$ alkylene bridges; $R^{6-7}$ are individually selected from the group consisting of alkyl, fluoroalkyl, cycloaliphatic, aryl, and heterocyclic containing a oxygen, or nitrogen atom; and X is either an oxygen, or nitrogen substituted with a hydrogen, an alkyl or an aryl group.

2. The metal containing complex of claim 1 structure A wherein M is selected from the group consisting of calcium, strontium, barium, scandium, yttrium, lanthanum, titanium, zirconium, vanadium, tungsten, manganese, cobalt, iron, nickel, ruthenium, zinc, copper, palladium, platinum, iridium, rhenium, and osmium.

3. The metal containing complex of claim 2 wherein M is selected from the group consisting of Ca, Sr, and Ba.

4. The metal containing complex of claim 3, wherein M is strontium, $R^1$ is t-butyl, $R^2$ is hydrogen, $R^3$ is methyl, $R^4$ is a $C_2$ alkylene bridge, and $R^5$ and $R^6$ are individually selected from the group consisting of methyl and ethyl.

5. The metal containing complex of claim 2 wherein M is selected from the group consisting of Fe, Co, and Ni.

6. The metal containing complex of claim 5 wherein M is cobalt, $R^1$ is selected from the group consisting of methyl and t-butyl, $R^2$ is hydrogen, $R^3$ is methyl, $R^4$ is selected from the group consisting of a $C_2$ alkylene bridge and a $C_3$ alkylene bridge, and $R^5$ and $R^6$ are methyl.

7. The metal containing complex of claim 5 wherein M is nickel, $R^1$ is selected from the group consisting of methyl and t-butyl, $R^2$ is hydrogen, $R^3$ is methyl, $R^4$ is selected from the group consisting of a $C_2$ alkylene bridge and a $C_3$ alkylene bridge, and $R^5$ and $R^6$ are methyl.

8. The metal containing complex of claim 2 wherein M is selected from the group consisting of Y and La.

9. The metal containing complex of claim 8 wherein $R^1$ is selected from the group consisting of $C_{1-5}$ alkyl, $R^2$ is selected from the group consisting of hydrogen, methyl, and ethyl, $R^3$ is selected from the group consisting of methyl and ethyl, $R^4$ is a $C_{2-3}$ alkylene bridge, and $R^5$ and $R^6$ are individually selected from the group consisting of methyl and ethyl.

10. The metal containing complex of claim 8 wherein M selected from the group consisting of Y and La, $R^1$ is t-butyl, $R^2$ is hydrogen, $R^3$ is methyl, $R^4$ is a $C_2$ alkylene bridge, and $R^5$ and $R^6$ are methyl.

11. The metal containing complex of claim 1 represented by the structure B:
wherein M is selected from the group consisting of titanium, zirconium, hafnium, vanadium, niobium, and tantalum.

12. The metal containing complex of claim 11 wherein $R^1$ is selected from the group consisting of $C_{1-5}$ alkyl, $R^2$ is selected from the group consisting of hydrogen, methyl, and ethyl, $R^3$ is selected from the group consisting of methyl and ethyl, $R^4$ is a $C_{2-3}$ alkylene bridge, $R^5$ and $R^6$ are individually selected from the group consisting of methyl and ethyl, and $R^7$ is selected the group consisting of methyl, ethyl, propyl, iso-propyl, n-butyl, sec-butyl, and tert-butyl.

13. The metal containing complex of claim 11 wherein M is Ti, $R^1$ is selected the group consisting of methyl and t-butyl, $R^2$ is hydrogen, $R^3$ is methyl, $R^4$ is a $C_2$ alkylene bridge, and $R^5$ and $R^6$ are methyl.

14. The metal-containing complex of claim 1 represented by structure C wherein M is selected from the group consisting of Ca, Sr, and Ba.

15. The metal containing complex of claim 14 wherein $R^1$ is selected from the group consisting of t-butyl and t-pentyl, $R^2$ is hydrogen, $R^3$ is methyl, $R^4$ and $R^5$ each are a $C_2$ alkylene bridge, $R^6$ and $R^7$ are individually selected from the group consisting of methyl and ethyl, and X is selected from the group consisting of oxygen and $NCH_3$.

16. The metal containing complex of claim 14 wherein M is Ba, $R^1$ is t-butyl, $R^2$ is hydrogen, $R^3$ is methyl, $R^4$ and $R^5$ each are a $C_2$ alkylene bridge, $R^6$ and $R^7$ are methyl, and $X=NCH_3$.

17. The metal containing complex of claim 1 dissolved in a solvent selected from the group consisting of glyme solvents having from 1 to 20 ethoxy —$(C_2H_4O)$—repeat units; $C_2$-$C_{12}$ alkanols, organic ethers selected from the group consisting of dialkyl ethers comprising $C_i$-$C_6$ alkyl moieties, $C_4$-$C_8$ cyclic ethers; $C_{12}$-$C_{60}$ crown $O_4$-$O_{20}$ ethers wherein the prefixed $C_i$ range is the number i of carbon atoms in the ether compound and the suffixed $O_i$ range is the number i of oxygen atoms in the ether compound; $C_6$-$C_{12}$ aliphatic hydrocarbons; $C_6$-$C_{18}$ aromatic hydrocarbons; organic esters; organic amines; and polyamines and organic amides.

18. The metal containing complex of claim 17 wherein the solvent is an organic amide selected from the group consisting N-methyl-2-pyrrolidinone, N-ethyl-2-pyrrolidinone, and N-cyclohexyl-2-pyrrolidinone.

19. A vapor deposition process for forming a conformal metal oxide thin film on a substrate wherein a precursor source and an oxygen containing agent are introduced to a deposition chamber and a metal oxide film deposited on a substrate, the improvement which comprises using the metal containing complex of claim 1 as said precursor source.

20. The process of claim 19 wherein the vapor deposition process is selected from the group consisting of chemical vapor deposition and atomic layer deposition.

21. The process of claim 19 wherein the oxygen containing agent is selected from the group consisting of water, $O_2$, $H_2O_2$, ozone and mixtures thereof.

22. A vapor deposition process for forming a conformal metal thin film on a substrate wherein a precursor source and a reducing agent are introduced to a deposition chamber and a metal film deposited on a substrate, the improvement which comprises using the metal containing complex of claim 1 as said precursor source.

23. The process of claim 22 wherein the reducing agent is selected from the group consisting of hydrogen, hydrazine, monoalkylhydrazine, dialkylhydrazine, ammonia, and mixtures thereof.

24. A vapor deposition process for forming a conformal metal oxide thin film on a substrate wherein a solution of precursor source and an oxygen containing agent are introduced to a deposition chamber and a metal oxide film deposited on a substrate, the improvement which comprises using a solution of comprised of the metal containing complex of claim 1 dissolved in a solvent selected from the group consisting of glyme solvents having from 1 to 20 ethoxy —$(C_2H_4O)$— repeat units; $C_2$-$C_{12}$ alkanols, organic ethers selected from the group consisting of dialkyl ethers comprising $C_1$-$C_6$ alkyl moieties, $C_4$-$C_8$ cyclic ethers; $C_{12}$-$C_{60}$ crown $O_4$-$O_{20}$ ethers wherein the prefixed $C_i$ range is the number i of carbon atoms in the ether compound and the suffixed $O_i$ range is the number i of oxygen atoms in the ether compound; $C_6$-$C_{12}$ aliphatic hydrocarbons; $C_6$-$C_{18}$ aromatic hydrocarbons; organic esters; organic amines; and polyamines and organic amides.

25. A vapor deposition process for forming a conformal metal thin film on a substrate wherein a solution of a precursor source and a reducing agent are introduced to a deposition chamber and a metal film deposited on a substrate, the improvement which comprises using a solution comprised of the metal containing complex of claim 1 dissolved in a solvent selected from the group consisting of glyme solvents having from 1 to 20 ethoxy —($C_2H_4O$)— repeat units; $C_2$-$C_{12}$ alkanols, organic ethers selected from the group consisting of dialkyl ethers comprising $C_1$-$C_6$ alkyl moieties, $C_4$-$C_8$ cyclic ethers; $C_{12}$-$C_{60}$ crown $O_4$-$O_{20}$ ethers wherein the prefixed $C_i$ range is the number i of carbon atoms in the ether compound and the suffixed $O_i$ range is the number i of oxygen atoms in the ether compound; $C_6$-$C_{12}$ aliphatic hydrocarbons; $C_6$-$C_{18}$ aromatic hydrocarbons; organic esters; organic amines; and polyamines and organic amides.

26. The metal containing complex of claim 3 wherein $R^1$ is selected from the group consisting of t-butyl and t-pentyl, $R^2$ is selected from the group consisting of hydrogen, methyl and ethyl, $R^3$ is selected from the group consisting of methyl and ethyl, $R^4$ is a $C_2$ alkylene bridge, and $R^5$ and $R^6$ are individually selected from the group consisting of methyl and ethyl.

27. The metal containing complex of claim 3 wherein M is strontium, $R^1$ is t-butyl, $R^2$ is hydrogen, $R^3$ is methyl, $R^4$ is a $C_2$ alkylene bridge, and $R^5$ and $R^6$ are ethyl.

28. The metal containing complex of claim 5 wherein $R^1$ is selected from the group consisting of $C_{1-6}$ alkyl, $R^2$ is selected from the group consisting of hydrogen, methyl, and ethyl, $R^3$ is selected from the group consisting of methyl and ethyl, $R^4$ is a $C_{2-3}$ alkylene bridge, and $R^5$ and $R^6$ are individually selected from the group consisting of methyl and ethyl.

29. The metal containing complex of claim 5 wherein M is cobalt, $R^1$ is t-butyl, $R^2$ is hydrogen, $R^3$ is methyl, $R^4$ is a $C_2$ alkylene bridge, and $R^5$ and $R^6$ are methyl.

30. The metal containing complex of claim 5 wherein M is cobalt, $R^1$ is methyl, $R^2$ is hydrogen, $R^3$ is methyl, $R^4$ is a $C_3$ alkylene bridge, and $R^5$ and $R^6$ are methyl.

31. The metal containing complex of claim 5 wherein M is cobalt, $R^1$ is t-butyl, $R^2$ is methyl, $R^4$ is a $C_3$ alkylene bridge, and $R^5$ and $R^6$ are methyl.

32. The metal containing complex of claim 5 wherein M is nickel, $R^1$ is t-butyl, $R^2$ is hydrogen, $R^3$ is methyl, $R^4$ is a $C_2$ alkylene bridge, and $R^5$ and $R^6$ are methyl.

33. The metal containing complex of claim 5 wherein M is nickel, $R^1$ is methyl, $R^2$ is hydrogen, $R^3$ is methyl, $R^4$ is a $C_3$ alkylene bridge, and $R^5$ and $R^6$ are methyl.

34. The metal containing complex of claim 5 wherein M is nickel, $R^1$ is t-butyl, $R^2$ is hydrogen, $R^3$ is methyl, $R^4$ is a $C_3$ alkylene bridge, and $R^5$ and $R^6$ are methyl.

35. The metal containing complex of claim 8 wherein M is Y, $R^1$ is t-butyl, $R^2$ is hydrogen, $R^3$ is methyl, $R^4$ is a $C_3$ alkylene bridge, and $R^5$ and $R^6$ are methyl.

36. The metal containing complex of claim 8 wherein M is La, $R^1$ is t-butyl, $R^2$ is hydrogen, $R^3$ is methyl, $R^4$ is a $C_2$ alkylene bridge, and $R^5$ and $R^6$ are methyl.

37. The metal containing complex of claim 8 wherein M is La, $R^1$ is t-butyl, $R^2$ is hydrogen, $R^3$ is methyl, $R^4$ is a $C_3$ alkylene bridge, and $R^5$ and $R^6$ are methyl.

38. The metal containing complex of claim 11 wherein M is Hf, $R^1$ is methyl, $R^2$ is hydrogen, $R^3$ is methyl, $R^4$ is a $C_2$ alkylene bridge, and $R^5$ and $R^6$ are methyl.

39. The metal containing complex of claim 11 wherein M is Zr, $R^1$ is methyl, $R^2$ is hydrogen, $R^3$ is methyl, $R^4$ is a $C_2$ alkylene bridge, and $R^5$ and $R^6$ are methyl.

40. The metal containing complex of claim 11 wherein M is Ti, $R^1$ is t-butyl, $R^2$ is hydrogen, $R^3$ is methyl, $R^4$ is a $C_2$ alkylene bridge, and $R^5$ and $R^6$ are methyl.

41. The metal containing complex of claim 11 wherein M is Hf, $R^1$ is t-butyl, $R^2$ is hydrogen, $R^3$ is methyl, $R^4$ is a $C_2$ alkylene bridge, and $R^5$ and $R^6$ are methyl.

42. The metal containing complex of claim 11 wherein M is Zr, $R^1$ is t-butyl, $R^2$ is hydrogen, $R^3$ is methyl, $R^4$ is a $C_2$ alkylene bridge, and $R^5$ and $R^6$ are methyl.

43. The metal containing complex of claim 4 wherein M is strontium, $R^1$ is t-butyl, $R^2$ is hydrogen, $R^3$ is methyl, $R^4$ is a $C_2$ alkylene bridge, and $R^5$ and $R^6$ are methyl.

44. The metal containing complex of claim 4 wherein M is strontium, $R^1$ is t-butyl, $R^2$ is hydrogen, $R^3$ is methyl, $R^4$ is a $C_2$ alkylene bridge, and $R^5$ is methyl and $R^6$ is ethyl.

45. The metal containing complex of claim 4 wherein M is strontium, $R^1$ is t-butyl, $R^2$ is hydrogen, $R^3$ is methyl, $R^4$ is a $C_2$ alkylene bridge, and $R^5$ and $R^6$ are ethyl.

* * * * *